United States Patent
Boeck et al.

(10) Patent No.: US 10,544,279 B2
(45) Date of Patent: Jan. 28, 2020

(54) PRODUCTION OF ESTER MIXTURES

(71) Applicant: Evonik Degussa GmbH, Essen (DE)

(72) Inventors: Florian Boeck, Muenster (DE);
Carsten Gehlen, Marl (DE); Michael Grass, Haltern am See (DE); Benjamin Woldt, Bochum (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/047,051

(22) Filed: Feb. 18, 2016

(65) Prior Publication Data

US 2016/0237244 A1  Aug. 18, 2016

(30) Foreign Application Priority Data

Feb. 18, 2015  (EP) .................................. 15155564

(51) Int. Cl.
| | |
|---|---|
| *C07C 69/82* | (2006.01) |
| *C07C 69/753* | (2006.01) |
| *C07C 69/704* | (2006.01) |
| *C08K 5/12* | (2006.01) |
| *C07C 67/08* | (2006.01) |

(52) U.S. Cl.
CPC ................ *C08K 5/12* (2013.01); *C07C 67/08* (2013.01)

(58) Field of Classification Search
CPC ........ C07C 67/03; C07C 67/035; C07C 67/08
See application file for complete search history.

(56) References Cited

U.S. PATENT DOCUMENTS

| | | | |
|---|---|---|---|
| 8,431,638 | B2 | 4/2013 | Grass et al. |
| 2014/0096703 | A1 | 4/2014 | Lee et al. |

FOREIGN PATENT DOCUMENTS

| | | |
|---|---|---|
| EP | 2 784 113 A1 | 10/2014 |
| KR | 10-2013-0035493 A | 4/2013 |
| WO | WO 2008/140177 A1 | 11/2008 |
| WO | WO 2011/115757 A1 | 9/2011 |

OTHER PUBLICATIONS

European Search Report dated Aug. 18, 2015 in Patent Application No. 15155564.6 (with English translation of categories of cited documents).

*Primary Examiner* — Wenwen Cai
(74) *Attorney, Agent, or Firm* — Oblon, McClelland, Maier & Neustadt, L.L.P.

(57) ABSTRACT

Ester mixtures comprising the esters $A(COOR^1)(COOR^1)_x$, $A(COOR^1)(COOR^2)_x$, $A(COOR^2)(COOR^1)_x$ and $A(COOR^2)(COOR^2)_x$, can be produced in a targeted way by processes in which acids $A(COOH)_{x+1}$ or derivatives thereof are reacted with an amount $(m_1+s_1)$ of $R^1OH$ and an amount $m_2$ of $R^2OH$, the reaction mixture being heated at boiling, the alcohol $R^1OH$ having a lower boiling point than the alcohol $R^2OH$, A being an aromatic, alicyclic or aliphatic radical, x being 1 or 2, and $R^1$ and $R^2$ independently of one another being substituted or unsubstituted aryl radicals or linear or branched, substituted or unsubstituted alkyl radicals having 3 to 20 carbon atoms, $m_1$ and $m_2$ corresponding to the mole equivalents of the alcohol radicals $OR^1$ and $OR^2$ to be introduced into $A(COOH)_{x+1}$ or derivatives thereof, and $s_1$ being greater than 0.

21 Claims, 1 Drawing Sheet

PRODUCTION OF ESTER MIXTURES

BACKGROUND OF THE INVENTION

Field of the Invention

The present invention relates to a process for producing an ester mixture, to the ester mixture produced in this way, to the use of the ester mixture as a plasticizer, and to compositions which comprise this ester mixture.

Discussion of the Background

The use of esters of terephthalic acid, phthalic acid, cyclohexanedicarboxylic acids, adipic acid, succinic acid, citric acid and other organic acids as plasticizers for polymers has been known for some considerable time. These esters are produced primarily by esterification of the acids or derivatives thereof with alcohols.

Depending on the acid used or on the acid derivative used and on the alcohol selected, there are significant variations in the properties of the resultant (unmixed) esters. The resulting esters are indeed suitable as plasticizers for a wide variety of applications but often, in addition to one or two very good properties, also have unfavourable properties, which may then severely restrict the use of the ester in question. For example, dioctyl phthalate, diisodecyl phthalate, diisononyl phthalate, trioctyl trimellitate and triisononyl trimellitate could be used usefully in the various high-temperature applications, since they exhibit high heat stability and low volatility. According to document US 2014/0096703 A1, however, their use in the area of these applications was subject to restrictions, since these esters had low compatibility with the polymers used for these applications. The dibutyl derivatives of these esters exhibited high compatibility with polymers, for example PVC, but were not suitable for high-temperature applications, on account of their low heat stability. In order to be able nevertheless to provide plasticizer systems which exhibit high heat stability in conjunction with high compatibility, document US 2014/0096703 A1 proposes the use of an ester mixture composed of $C_8$ and $C_{10}$ esters of terephthalic acid comprising not only the unmixed esters but also the mixed ester which has a $C_8$ and a $C_{10}$-alcohol radical.

Document KR 2013/0035493 A sets out the problem that dibutyl terephthalate, while having a high rate on penetration into the resin and on melting, nevertheless exhibited an undesirably high migration loss, whereas for diethylhexyl terephthalate there was virtually no migration loss, but penetration into the resin, and melting, took an unacceptably long time. For improvement, that document also proposes using ester mixtures comprising the mixed ester containing a $C_4$ and a $C_8$ alcohol radical.

Document WO 2008/140177 A1 proposes the preparation of ester mixtures composed of $C_8$ and $C_9$ esters of terephthalic acid, which again also include the mixed ester, and describes how an improvement was possible in the processing qualities of the plasticizer preparations through the variation of the ratios of the individual esters in the ester mixture.

Also known are ester mixtures comprising mixed esters prepared from cyclohexanedicarboxylic acids with different alcohols (WO 2011/115757 A1).

Also known are mixtures of citric esters including not only the corresponding unmixed esters but also mixed esters with $C_5$ and $C_9$ alcohol radicals (U.S. Pat. No. 8,431,638 B2).

These ester mixtures are provided in the related art—irrespective of their parent structure—by the esterification of the corresponding acids or acid derivatives with an alcohol mixture which provides the alcohol radicals of the unmixed esters and of the mixed ester or mixed esters.

As is, for example, shown in document WO 2008/140177 A1, however, it is not possible to set the distribution of the resultant esters in a targeted way by means of the composition of the alcohol mixture. Accordingly, the ester mixtures produced in the examples of that document do not contain the $C_8$ and $C_9$ alcohol radicals in the proportion in which these radicals are present in the alcohol mixture used and probably also the proportion in which it was intended that they should be introduced into the system. The $C_8/C_8$ esters, the $C_8/C_9$ esters and the $C_9/C_9$ esters as well are not formed in the molar ratios expected on the basis of statistical considerations, but instead in ratios which deviate markedly therefrom. In Example 1 of document WO 2008/140177 A1, with a statistical expectation value of 25:50:25 (assumption: equimolar incorporation of the alcohol radicals), the molar ratio obtained for the esters is 10:54:36, which corresponds to an uncontrollable deviation by (|25−10|+|50−54|+|25−36|=) 30 points (the calculation of the deviation in points will be elucidated later on in the text). While in this example the two alcohols are indeed used in a molar ratio of 1:1, the resulting ester mixture contains the two alcohol radicals in a molar ratio of 37:63. The document ascribes these deviations from the statistical expectation value to the differing reaction rates of the individual esterification reactions.

This problem of the "uncontrollability" of the ester mixture compositions in the case of production by esterification of terephthalic acid is resolved in document KR 2013/0035493 A by separately preparing the esters of the mixture and blending them in the desired ratio. The document, however, includes no disclosure as to how it is possible to produce a mixed ester separately without at the same time forming the two unmixed diesters. Nor does this appear possible at commercially acceptable cost and effort. The provision of the pure mixed ester would have to be accomplished by removal thereof from the unmixed esters during a separation step. If this purified mixed ester is then to be blended with the two unmixed esters, in accordance with the disclosure content of document KR 2013/0035493 A, then the production of an ester mixture requires the performance, for example, of at least three esterification reactions and one subsequent blending—a procedure inconvenient and costly in terms of both apparatus and time.

A different pathway is described by document U.S. Pat. No. 8,431,638 B2 for the production of mixed citric esters. Mixtures comprising these esters can be produced by subjecting citric acid pentyl esters to the transesterification with citric acid nonyl esters. This procedure nevertheless requires three separate process steps: two esterifications and one transesterification.

SUMMARY OF THE INVENTION

It is an object of the present invention, then to overcome a number, preferably all, of the above-stated disadvantages of the related art. With preference the intention was to develop a process in which it is possible to produce mixtures comprising mixed esters and unmixed esters with a predetermined quantitative distribution of the esters in a targeted way, with as little as possible a complexity and cost in terms of apparatus and of time.

These and other objects are achieved by a process for producing an ester mixture, comprising:

reacting $A(COOH)_{x+1}$ or derivatives thereof which contain no ester group COOR having a radical R whose alcohol ROH has a higher boiling point at a defined pressure than the alcohol $R^1OH$ of the radical $R^1$ at the same pressure, with an amount $(m_1+s_1)$ of $R^1OH$ and an amount $m_2$ of $R^2OH$ in a reaction mixture, heating the reaction mixture at boiling, to obtain the ester mixture comprising $A(COOR^1)(COOR^1)_x$, $A(COOR^1)(COOR^2)_x$, $A(COOR^2)(COOR^1)_x$ and $A(COOR^2)(COOR^2)_x$, wherein A is an aromatic, alicyclic or aliphatic radical, x is 1 or 2, $R^1$ and $R^2$ independently of one another are substituted or unsubstituted aryl radicals or linear or branched, substituted or unsubstituted alkyl radicals having 3 to 20 carbon atoms, the alcohol $R^1OH$ having a lower boiling point at a defined pressure than the alcohol $R^2OH$ at the same pressure, $m_1$ and $m_2$ correspond to the mole equivalents of the alcohol radicals $OR^1$ and $OR^2$ to be introduced into $A(COOH)_{x+1}$ or derivatives thereof, and $s_1$ is greater than 0.

The present invention also relates to an ester mixture produced by the above process.

In another embodiment, the present invention provides for a polymer plasticizer, comprising:

the above ester mixture.

The present invention also relates to an adhesive, sealant, coating material, paint, ink, plastisol, foam, synthetic leather, floorcovering, roofing membrane, underbody protection, fabric coating, cable, wire insulation, hose, extruded article, film, automotive interior article, wallcovering, liquid ink, toy, contact sheet, food packaging or medical article, comprising:

the above polymer plasticizer.

In yet another embodiment, the present invention relates to a composition, comprising:

the above ester mixture; and one or more polymers selected from the group consisting of polyvinyl chloride, copolymers of vinyl chloride with vinyl acetate or with butyl acrylate, polyalkyl methacrylate (PAMA), polyvinyl butyral (PVB), polyurethane, polysulphides, polylactic acid (PLA), polyhydroxybutyral (PHB) and nitrocellulose.

DETAILED DESCRIPTION OF THE INVENTION

All ranges below include the lowest and highest value of the range as well as all subvalues therebetween.

A subject of the present invention is a process for producing ester mixtures comprising $A(COOR^1)(COOR^1)_x$, $A(COOR^1)(COOR^2)_x$, $A(COOR^2)(COOR^1)_x$ and $A(COOR^2)(COOR^2)_x$ by reaction of $A(COOH)_{x+1}$ or derivatives thereof which contain no ester groups COOR having a radical R whose alcohol ROH has a higher boiling point at a defined pressure than the alcohol $R^1OH$ of the radical $R^1$ at the same pressure, with an amount $(m_1+s_1)$ of $R^1OH$ and an amount $m_2$ of $R^2OH$, the reaction mixture being heated at boiling, and A is an aromatic, alicyclic or aliphatic radical, X is 1 or 2, $R^1$ and $R^2$ independently of one another are substituted or unsubstituted aryl radicals or linear or branched, substituted or unsubstituted alkyl radicals having 3 to 20 carbon atoms, the alcohol $R^1OH$ having a lower boiling point at a defined pressure than the alcohol $R^2OH$ at the same pressure, $m_1$ and $m_2$ correspond to the mole equivalents of the alcohol radicals $OR^1$ and $OR^2$ to be introduced into $A(COOH)_{x+1}$ or derivatives thereof, and $s_1$ is greater than 0.

For x=1 the esters $A(COOR^1)(COOR^2)_x$ and $A(COOR^2)(COOR^1)_x$ are one and the same compound.

In one embodiment, in the process the acid $A(COOH)_{x+1}$ is esterified to give the esters $A(COOR^1)(COOR^1)_x$, $A(COOR^1)(COOR^2)_x$, $A(COOR^2)(COOR^1)_x$ and $A(COOR^2)(COOR^2)_x$.

In another embodiment, in the process the ester $A(COOR)_{x+1}$ is transesterified to give the esters $A(COOR^1)(COOR^1)_x$, $A(COOR^1)(COOR^2)_x$, $A(COOR^2)(COOR^1)_x$ and $A(COOR^2)(COOR^2)_x$. In this case the alcohol ROH of the radical R has a lower boiling point at a defined pressure than the alcohol $R^1OH$ of the radical $R^1$ at the same pressure.

In a further embodiment, in the process an anhydride of the acid $A(COOH)_{x+1}$ is esterified to give the esters $A(COOR^1)(COOR^1)_x$, $A(COOR^1)(COOR^2)_x$, $A(COOR^2)(COOR^1)_x$ and $A(COOR^2)(COOR^2)_x$.

With preference at least 95 mol %, preferably at least 98 mol %, more preferably at least 99 mol % and more particularly 100 mol % of the alcohol radicals introduced into $A(COOH)_{x+1}$ or derivatives thereof in the course of the process of the invention become part of an ester function.

In the process of the invention, $A(COOH)_{x+1}$ or a derivative thereof is reacted with a mixture of the alcohols $R^1OH$ and $R^2OH$. Surprisingly it has been found that the composition of the resulting ester mixture comprising the unmixed esters $A(COOR^1)(COOR^1)_x$ and $A(COOR^2)(COOR^2)_x$ and also the mixed esters $A(COOR^1)(COOR^2)_x$ and $A(COOR^2)(COOR^1)_x$ can then be adjusted in a targeted manner—within the bounds of the statistics resulting for the case of the complete incorporation of alcohol radicals $OR^2$—when the lower-boiling alcohol $R^1OH$ is used in excess relative to the alcohol radicals $OR^1$ to be introduced into $A(COOH)_{x+1}$ or derivatives thereof, but the amount of the higher-boiling alcohol $R^2OH$ used corresponds to the amount of the alcohol radicals $OR^2$ to be introduced. Controlling the ester mixture composition is not possible in contrast, if an excess of the alcohol mixture ($R^1OH+R^2OH$) in relation to the alcohol radicals that are to be introduced is used in an esterification or transesterification, or if $A(COOH)_{x+1}$ or a derivative thereof is reacted with a mixture of the alcohols $R^1OH$ and $R^2OH$, the higher-boiling alcohol $R^2OH$ being used in excess relative to the alcohol radicals $OR^2$ to be introduced into $A(COOH)_{x+1}$ or derivatives thereof.

Accordingly it is possible by means of the process of the invention to provide ester mixtures in which the different alcohol radicals are present in a predetermined quantitative distribution and in which, moreover, the quantitative distribution of the esters present can be controlled in a targeted way—within the bounds of the statistics stated above. It is therefore possible for ester mixtures to be provided whose composition exhibits smaller deviations from the ester distribution arising on the basis of the statistics than ester mixtures produced according to uncontrolled processes described in the related art.

For x=1, the statistical expectation values for the ester mixture composition are those shown in Table 1.

TABLE 1 statistical expectation values of ester mixture composition for x = 1

| Input Ratio $R^1OH$ to $R^2OH$ ($m_1$:$m_2$) | | Expected amount $A(COOR^1)_2$ | Expected amount $A(COOR^1)(COOR^2)$ + $A(COOR^2)(COOR^1)$ | Expected amount $A(COOR^2)_2$ |
|---|---|---|---|---|
| $m_1$ | $m_2$ | [mol %] | [mol %] | [mol %] |
| 9 | 1 | 81 | 18 | 1 |
| 8 | 2 | 64 | 32 | 4 |
| 7 | 3 | 49 | 42 | 9 |
| 6 | 4 | 36 | 48 | 16 |
| 5 | 5 | 25 | 50 | 25 |
| 4 | 6 | 16 | 48 | 36 |
| 3 | 7 | 9 | 42 | 49 |
| 2 | 8 | 4 | 32 | 64 |
| 1 | 9 | 1 | 18 | 81 |

Deviation in the ester mixture composition from the quantitative distribution of the esters in the ester mixture as it results from statistical considerations can be quantified by summing all of the amounts for differences between the statistical expectation value that arises on assumption of complete incorporation of the alcohol radicals $OR^2$ and the actual molar fraction of each individual ester in the ester mixture in the event that the sum total of the molar fractions of the aforementioned esters in the ester mixture adds up to 100.

The process of the invention is successful, for example, in providing, from 5 mol of dimethyl terephthalate, 3.5 mol of isopentanol and 9 mol of isononanol, in a targeted way, an ester mixture in which the molar distribution of the esters present deviates by only 1 point from the statistical expectation value and where the fraction of the pentyl radicals in the ester mixture is within 0.3% of the intended pentyl fraction.

In the process of the invention, the radical A may stand for aromatic, alicyclic or aliphatic radicals. In one embodiment, A is an aliphatic radical having 4 to 12 carbon atoms that comprises 2 or 3 acid functions and optionally carries further functional groups. In another embodiment, A is an unsaturated alkyl radical which contains 4 to 12 carbon atoms, having 2 or 3 acid functions and optionally carrying further functional groups. In a further embodiment, A is an alicyclic radical which has 4 to 8 carbon atoms, attached to which are 2 or 3 carboxylic acid functions and optionally further functional radicals. In a further embodiment, A is an aromatic radical having 2 or 3 carboxylic acid functions and optionally further functional groups.

The ester mixture produced by means of the process of the invention is preferably an ester mixture of phthalic acid, terephthalic acid, isophthalic acid, 1,2-, 1,3- or 1,4-cyclohexanedicarboxylic acid, adipic acid, sebacic acid, maleic acid, succinic acid, furandicarboxylic acid or citric acid.

The radicals $R^1$ and $R^2$ may be selected independently of one another from substituted or unsubstituted aryl radicals, for example benzyl radicals, and linear or branched, substituted or unsubstituted alkyl radicals having 3 to 20 carbon atoms, provided that the alcohol $R^1OH$ has a lower boiling point at a defined pressure than the alcohol $R^2OH$ at the same pressure. In one embodiment the radicals $R^1$ and $R^2$ are selected from linear or branched, substituted or unsubstituted alkyl radicals having 3 to 20 carbon atoms, with preferably one of the radicals, $R^1$ or $R^2$, or both radicals $R^1$ and $R^2$, comprising further functional groups, examples being one or more multiple bonds, ether groups, aldehyde groups, ketone groups, hydroxyl groups and/or halide groups. In another embodiment, the radicals $R^1$ and $R^2$ independently of one another are selected from alkyl radicals which contain 3 to 20, preferably 4 to 15 and more particularly 5 to 11 carbon atoms, the alkyl radicals preferably having no further functional groups, including multiple bonds. Preferably $R^1$ and $R^2$ independently of one another are selected from propyl, butyl, tert-butyl, isobutyl, 2-methylbutyl, 3-methylbutyl, n-pentyl, isopentyl, hexyl, heptyl, isoheptyl, octyl, isooctyl, 2-ethylhexyl, nonyl, n-nonyl, isononyl, decyl, isodecyl, 2-propylheptyl, undecyl and tridecyl radicals.

With preference in this case the radical $R^1$ is selected from propyl, butyl, tert-butyl, isobutyl, 2-methylbutyl, 3-methylbutyl, n-pentyl, isopentyl, hexyl, heptyl and isoheptyl radicals and at the same time the radical $R^2$ is selected from n-pentyl, isopentyl, hexyl, heptyl, isoheptyl, octyl, isooctyl, 2-ethylhexyl, nonyl, n-nonyl, isononyl, decyl, isodecyl, 2-propylheptyl, undecyl and tridecyl radicals, but with the proviso that the alcohol $R^1OH$ of the radical $R^1$ has a lower boiling point at a defined pressure than the alcohol $R^2OH$ of the radical $R^2$ at the same pressure.

It has emerged that the process can be carried out with particularly small deviations from the molar ratio of the unmixed esters and mixed esters formed that is predetermined statistically on the basis of the stoichiometric input amounts $m_1$ and $m_2$ if the boiling points of the alcohols $R^1OH$ and $R^2OH$ differ by at least 10° C., preferably by at least 25° C. and more particularly by at least 40° C. The alcohol $R^1OH$ at 1013 hPa preferably has a boiling point which is lower by at least 10° C., more preferably by at least 20° C., more preferably by at least 30° C., with preference by at least 40° C., with particular preference by at least 50° C. and more particularly by at least 60° C. than the alcohol $R^2OH$ at the same pressure.

Where the alcohol $R^1OH$ and/or the alcohol $R^2OH$ are/is an isomer mixture, this fact is characterized in the context of this text—and in the manner usual within industrial chemistry—by the prefix "iso". Isomer mixtures do not have a precise boiling point, but instead possess a boiling range. In the case of isomer mixtures, the difference in the boiling points for the purposes of the present invention is determined by forming the difference between the lower boiling range limit of the higher-boiling alcohol and the upper boiling range limit of the lower-boiling alcohol.

With preference, the alcohols $R^1OH$ and $R^2OH$ are used at a ratio to one another in the process of the invention such that the ratio of $m_1$ to $m_2$ ($m_1$:$m_2$) is in the range from 1:9 to 9:1, preferably in the range from 2:8 to 8:2, more preferably in the range from 3:7 to 7:3 and more particularly in the range from 4:6 to 6:4. If the alcohols $R^1OH$ and $R^2OH$ are used in a ratio $m_1$:$m_2$ of greater than 1.5:8.5, preferably greater than 2:8 and more particularly greater than 2.5:7.5, it is possible to obtain ester mixtures which relative to $A(COOR^2)(COOR^2)_x$ have much more favourable, i.e. lower, gelling temperatures and at the same time are characterized by a lower and hence improved volatility relative to $A(COOR^1)(COOR^1)_x$. Ester mixtures which can be processed to particularly good effect with polymers, for example PVC, may be obtained if the alcohols $R^1OH$ and $R^2OH$ are used in a ratio $m_1:m_2$ which is greater than 1.5:8.5, preferably greater than 2:8 and more particularly greater than 2.5:7.5. Ester mixtures which are suitable for producing compositions comprising ester mixture and polymer and possessing good storage qualities can be obtained if the alcohols $R^1OH$ and $R^2OH$ are used in a ratio $m_1:m_2$ of less than 8:2, preferably less than 7.5:2.5 and particularly less than 7:3. A further improvement in the properties in the area of volatility becomes possible if the alcohols $R^1OH$ and $R^2OH$ are used in a ratio $m_1:m_2$ of less than 4:6, preferably less than 3.5:6.5, more preferably less than 3:7, very preferably less than 2.5:7.5, with further preference less than 2:8 and more particularly less than 1.5:8.5. In the formation of all of these ratios, the "excess amount" $s_1$ of $R^1OH$ is disregarded.

The amount $s_1$ of $R^1OH$ that goes beyond the amount $m_1$ of the alcohol functions $OR^1$ to be introduced into $A(COOH)_{x+1}$ or derivatives thereof may act as solvent in the process of the invention. If water is formed in the process of the invention, then the amount $s_1$ of $R^1OH$ acts preferably as an azeotrope former for the water, which can be distilled off with $R^1OH$ as an azeotropic mixture. The amount $s_1$ is preferably less than $m_1+m_2$, with particular preference less than $0.6 \cdot (m_1+m_2)$, preferably less than $0.5 \cdot (m_1+m_2)$, more preferably less than $0.4 \cdot (m_1+m_2)$, with further preference less than $0.3 \cdot (m_1+m_2)$ and more particularly preferably less than $0.25 \cdot (m_1+m_2)$. If the amount $s_1$ is greater than $0.05 \cdot (m_1+m_2)$, preferably greater than $0.10 \cdot (m_1+m_2)$, more preferably greater than $0.15 \cdot (m_1+m_2)$ and more particularly greater than $0.20 \cdot (m_1+m_2)$, this constitutes a preferred embodiment of the process of the invention. The amount $s_1$ is preferably less than $(m_1+m_2)$, with preference less than $0.6 \cdot (m_1+m_2)$, more preferably less than $0.5 \cdot (m_1+m_2)$ and more particularly less than $0.4 \cdot (m_1+m_2)$ and at the same time preferably greater than $0.05 \cdot (m_1+m_2)$, more preferably greater than $0.10 \cdot (m_1+m_2)$ and more particularly greater than $0.15 \cdot (m_1+m_2)$.

Employed preferably as terephthalic acid derivative in the process of the invention is dimethyl terephthalate.

A preferred subject of the present invention is a process for producing ester mixtures comprising dipentyl terephthalate, diisononyl terephthalate and pentyl isononyl) terephthalate by reaction of terephthalic acid or derivatives thereof which contain no ester groups COOR with a radical R whose alcohol ROH has a higher boiling point at a defined pressure than pentanol at the same pressure, with an amount $(m_1+s_1)$ of pentanol and an amount $m_2$ of isononanol, the reaction mixture being heated at boiling and
  $m_1$ and $m_2$ corresponding to the mole equivalents of the alcohol radicals of pentanol and isononanol that are to be introduced into the terephthalic acid or derivatives thereof, and
  $s_1$ being greater than 0 and being more particularly in the range from 0.05 to 0.60 times $(m_1+m_2)$.

A preferred subject of the present invention is a process for producing ester mixtures comprising dipentyl terephthalate, dipropylheptyl terephthalate and pentylpropylheptyl terephthalate by reaction of terephthalic acid or derivatives thereof which contain no ester groups COOR with a radical R whose alcohol ROH has a higher boiling point at a defined pressure than pentanol at the same pressure, with an amount $(m_1+s_1)$ of pentanol and an amount $m_2$ of propylheptanol, the reaction mixture being heated at boiling and
  $m_1$ and $m_2$ corresponding to the mole equivalents of the alcohol radicals of pentanol and propylheptanol that are to be introduced into the terephthalic acid or derivatives thereof, and
  $s_1$ being greater than 0 and being more particularly in the range from 0.05 to 0.60 times $(m_1+m_2)$.

A preferred subject of the present invention is a process for producing an ester mixture of the 1,2-, 1,3- or 1,4-esters of cyclohexanedicarboxylic acid, comprising dipentyl cyclohexanedicarboxylate, diisononyl cyclohexanedicarboxylate and pentyl isononyl cyclohexanedicarboxylate by reaction of 1,2-, 1,3- or 1,4-cyclohexanedicarboxylic acid or derivatives thereof which contain no ester groups COOR with a radical R whose alcohol ROH has a higher boiling point at a defined pressure than pentanol at the same pressure, with an amount $(m_1+s_1)$ of pentanol and an amount $m_2$ of isononanol, the reaction mixture being heated at boiling and
  $m_1$ and $m_2$ corresponding to the mole equivalents of the alcohol radicals of pentanol and isononanol that are to be introduced into the 1,2-, 1,3- or 1,4-cyclohexanedicarboxylic acid or derivatives thereof, and
  $s_1$ being greater than 0 and being more particularly in the range from 0.05 to 0.60 times $(m_1+m_2)$.

A preferred subject of the present invention is a process for producing an ester mixture of the 1,2-, 1,3- or 1,4-esters of cyclohexanedicarboxylic acid, comprising dipentyl cyclohexanedicarboxylate, dipropylheptyl cyclohexanedicarboxylate and pentyl propylheptyl cyclohexanedicarboxylate by reaction of 1,2-, 1,3- or 1,4-cyclohexanedicarboxylic acid or derivatives thereof which contain no ester groups COOR with a radical R whose alcohol ROH has a higher boiling point at a defined pressure than pentanol at the same pressure, with an amount $(m_1+s_1)$ of pentanol and an amount $m_2$ of propylheptanol, the reaction mixture being heated at boiling and
  $m_1$ and $m_2$ corresponding to the mole equivalents of the alcohol radicals of pentanol and propylheptanol that are to be introduced into the 1,2-, 1,3- or 1,4-cyclohexanedicarboxylic acid or derivatives thereof, and
  $s_1$ being greater than 0 and being more particularly in the range from 0.05 to 0.60 times $(m_1+m_2)$.

A preferred subject of the present invention is a process for producing ester mixtures comprising dipentyl succinate, diisononyl succinate and pentyl isononyl succinate by reaction of succinic acid or derivatives thereof which contain no ester groups COOR with a radical R whose alcohol ROH has a higher boiling point at a defined pressure than pentanol at the same pressure, with an amount $(m_1+s_1)$ of pentanol and an amount $m_2$ of isononanol, the reaction mixture being heated at boiling and
  $m_1$ and $m_2$ corresponding to the mole equivalents of the alcohol radicals of pentanol and isononanol that are to be introduced into the succinic acid or derivatives thereof, and
  $s_1$ being greater than 0 and being more particularly in the range from 0.05 to 0.60 times $(m_1+m_2)$.

A preferred subject of the present invention is a process for producing ester mixtures comprising dipentyl succinate, dipropylheptyl succinate and pentyl propylheptyl succinate by reaction of succinic acid or derivatives thereof which contain no ester groups COOR with a radical R whose alcohol ROH has a higher boiling point at a defined pressure than pentanol at the same pressure, with an amount $(m_1+s_1)$ of pentanol and an amount $m_2$ of propylheptanol, the reaction mixture being heated at boiling and
  $m_1$ and $m_2$ corresponding to the mole equivalents of the alcohol radicals of pentanol and propylheptanol that are to be introduced into the succinic acid or derivatives thereof, and $s_1$ being greater than 0 and being more particularly in the range from 0.05 to 0.60 times ($m_1+m_2$).

A preferred subject of the present invention is a process for producing ester mixtures comprising tripentyl citrate, diisononyl pentyl citrate, dipentyl isononyl citrate and triisononyl citrate by reaction of citric acid or derivatives thereof which contain no ester groups COOR with a radical R whose alcohol ROH has a higher boiling point at a defined pressure than pentanol at the same pressure, with an amount ($m_1+s_1$) of pentanol and an amount $m_2$ of isononanol, the reaction mixture being heated at boiling and $m_1$ and $m_2$ corresponding to the mole equivalents of the alcohol radicals of pentanol and isononanol that are to be introduced into the citric acid or derivatives thereof, and $s_1$ being greater than 0 and being more particularly in the range from 0.05 to 0.60 times ($m_1+m_2$).

A preferred subject of the present invention is a process for producing ester mixtures comprising tripentyl citrate, dipropylheptyl pentyl propylheptyl citrate, dipentyl propylheptyl citrate and tripropylheptyl citrate by reaction of citric acid or derivatives thereof which contain no ester groups COOR with a radical R whose alcohol ROH has a higher boiling point at a defined pressure than pentanol at the same pressure, with an amount ($m_1+s_1$) of pentanol and an amount $m_2$ of propylheptanol, the reaction mixture being heated at boiling and $m_1$ and $m_2$ corresponding to the mole equivalents of the alcohol radicals of pentanol and propylheptanol that are to be introduced into the citric acid or derivatives thereof, and $s_1$ being greater than 0 and being more particularly in the range from 0.05 to 0.60 times ($m_1+m_2$).

The isononanol used in the process of the invention, more particularly the isononanol used in these embodiments, preferably has an average degree of branching of 1.0 to 2.2. The average degree of branching here is determined as described in document US 2010/305255 A1. In another embodiment, the isononanol used in the process of the invention, more particularly the isononanol used in above embodiments, contains less than 25 mol %, more particularly less than 15 mol %, of alcohols having a number of carbon atoms of smaller than or greater than 9. More preferably the isononanol used in the process of the invention, more particularly the isononanol used in these embodiments has an average degree of branching of 1.0 to 2.2 and at the same time contains less than 25 mol %, more particularly less than 15 mol %, of alcohols having a number of carbon atoms of smaller than or greater than 9.

Independently of this, the process of the invention, more particularly the embodiments described above, preferably use esters which contain n-pentyl, 2-methylbutyl and/or 3-methylbutyl radicals. In one preferred embodiment the pentyl radicals in the above-described embodiments are isomer mixtures and are therefore isopentyl radicals. With preference the fraction of the n-pentyl radicals, based on all of the pentyl radicals present, is at least 10 mol % or 20 mol %, preferably at least 30 mol %, more preferably at least 40 mol %, very preferably at least 50 mol % and more particularly at least 60 mol %, with the possible associated advantage of a lower viscosity which is therefore more favourable for the processing of the plastisols. In one preferred embodiment the fraction of the n-pentyl radicals, based on all of the pentyl radicals present, is between 10 and 90 mol %, preferably 20 to 80 mol % and more particularly 30 to 70 mol %.

The propylheptyl radicals are preferably 2-propylheptyl radicals.

A preferred subject of the present invention is a process for producing ester mixtures comprising dibutyl terephthalate, dioctyl terephthalate and butyl octyl terephthalate by reaction of terephthalic acid or derivatives thereof which contain no ester groups COOR with a radical R whose alcohol ROH has a higher boiling point at a defined pressure than butanol at the same pressure, with an amount ($m_1+s_1$) of butanol and an amount $m_2$ of octanol, the reaction mixture being heated at boiling and $m_1$ and $m_2$ corresponding to the mole equivalents of the alcohol radicals of butanol and octanol that are to be introduced into the terephthalic acid or derivatives thereof, and $s_1$ being greater than 0 and being more particularly in the range from 0.05 to 0.60 times ($m_1+m_2$).

Preferably here the octyl radicals are ethylhexyl radicals, more particularly 2-ethylhexyl radicals, and/or the butyl radicals are n-butyl radicals.

A preferred subject of the present invention is a process for producing ester mixtures comprising dinonyl terephthalate, didecyl terephthalate and nonyl decyl terephthalate by reaction of terephthalic acid or derivatives thereof which contain no ester groups COOR with a radical R whose alcohol ROH has a higher boiling point at a defined pressure than nonanol at the same pressure, with an amount ($m_1+s_1$) of nonanol and an amount $m_2$ of decanol, the reaction mixture being heated at boiling and $m_1$ and $m_2$ corresponding to the mole equivalents of the alcohol radicals of nonanol and decanol that are to be introduced into the terephthalic acid or derivatives thereof, and $s_1$ being greater than 0 and being more particularly in the range from 0.05 to 0.60 times ($m_1+m_2$).

The nonyl radicals here are preferably isononyl radicals and/or the decyl radicals here are preferably propylheptyl radicals, more particularly 2-propylheptyl radicals.

A preferred subject of the present invention is a process for producing ester mixtures comprising dioctyl terephthalate, didecyl terephthalate and octyl decyl terephthalate by reaction of terephthalic acid or derivatives thereof which contain no ester groups COOR with a radical R whose alcohol ROH has a higher boiling point at a defined pressure than octanol at the same pressure, with an amount ($m_1+s_1$) of octanol and an amount $m_2$ of decanol, the reaction mixture being heated at boiling and $m_1$ and $m_2$ corresponding to the mole equivalents of the alcohol radicals of octanol and decanol that are to be introduced into the terephthalic acid or derivatives thereof, and $s_1$ being greater than 0 and being more particularly in the range from 0.05 to 0.60 times ($m_1+m_2$).

The octyl radicals here are preferably ethylhexyl radicals, more particularly 2-ethylhexyl radicals and/or the decyl radicals here are preferably propylheptyl radicals, more particularly 2-propylheptyl radicals.

A preferred subject of the present invention is a process for producing ester mixtures comprising diheptyl terephthalate, dinonyl terephthalate and heptyl nonyl terephthalate by reaction of terephthalic acid or derivatives thereof which contain no ester groups COOR with a radical R whose alcohol ROH has a higher boiling point at a defined pressure than heptanol at the same pressure, with an amount ($m_1+s_1$) of heptanol and an amount $m_2$ of nonanol, the reaction mixture being heated at boiling and $m_1$ and $m_2$ corresponding to the mole equivalents of the alcohol radicals of heptanol and nonanol that are to be introduced into the terephthalic acid or derivatives thereof, and $s_1$ being greater than 0 and being more particularly in the range from 0.05 to 0.60 times $(m_1+m_2)$.

The nonyl radicals here are preferably isononyl radicals and/or the heptyl radicals here are preferably isoheptyl radicals.

A preferred subject of the present invention is a process for producing an ester mixture of the 1,2-, 1,3- or 1,4-esters of cyclohexanedicarboxylic acid, comprising dibutyl cyclohexanedicarboxylate, dioctyl cyclohexanedicarboxylate and butyl octyl cyclohexanedicarboxylate by reaction of 1,2-, 1,3- or 1,4-cyclohexanedicarboxylic acid or derivatives thereof which contain no ester groups COOR with a radical R whose alcohol ROH has a higher boiling point at a defined pressure than butanol at the same pressure, with an amount $(m_1+s_1)$ of butanol and an amount $m_2$ of octanol, the reaction mixture being heated at boiling and $m_1$ and $m_2$ corresponding to the mole equivalents of the alcohol radicals of butanol and octanol that are to be introduced into the 1,2-, 1,3- or 1,4-cyclohexanedicarboxylic acid or derivatives thereof, and $s_1$ being greater than 0 and being more particularly in the range from 0.05 to 0.60 times $(m_1+m_2)$.

The octyl radicals here are preferably ethylhexyl radicals, more particularly 2-ethylhexyl radicals and/or the butyl radicals here are preferably n-butyl radicals.

A preferred subject of the present invention is a process for producing an ester mixture of the 1,2-, 1,3- or 1,4-esters of cyclohexanedicarboxylic acid, comprising dinonyl cyclohexanedicarboxylate, didecyl cyclohexanedicarboxylate and nonyl decyl cyclohexanedicarboxylate by reaction of 1,2-, 1,3- or 1,4-cyclohexanedicarboxylic acid or derivatives thereof which contain no ester groups COOR with a radical R whose alcohol ROH has a higher boiling point at a defined pressure than nonanol at the same pressure, with an amount $(m_1+s_1)$ of nonanol and an amount $m_2$ of decanol, the reaction mixture being heated at boiling and $m_1$ and $m_2$ corresponding to the mole equivalents of the alcohol radicals of nonanol and decanol that are to be introduced into the 1,2-, 1,3- or 1,4-cyclohexanedicarboxylic acid or derivatives thereof, and $s_1$ being greater than 0 and being more particularly in the range from 0.05 to 0.60 times $(m_1+m_2)$.

The nonyl radicals here are preferably isononyl radicals and/or the decyl radicals here are preferably propylheptyl radicals, more particularly 2-propylheptyl radicals.

A preferred subject of the present invention is a process for producing an ester mixture of the 1,2-, 1,3- or 1,4-esters of cyclohexanedicarboxylic acid, comprising dioctyl cyclohexanedicarboxylate, didecyl cyclohexanedicarboxylate and octyl decyl cyclohexanedicarboxylate by reaction of 1,2-, 1,3- or 1,4-cyclohexanedicarboxylic acid or derivatives thereof which contain no ester groups COOR with a radical R whose alcohol ROH has a higher boiling point at a defined pressure than octanol at the same pressure, with an amount $(m_1+s_1)$ of octanol and an amount $m_2$ of decanol, the reaction mixture being heated at boiling and $m_1$ and $m_2$ corresponding to the mole equivalents of the alcohol radicals of octanol and decanol that are to be introduced into the 1,2-, 1,3- or 1,4-cyclohexanedicarboxylic acid or derivatives thereof, and $s_1$ being greater than 0 and being more particularly in the range from 0.05 to 0.60 times $(m_1+m_2)$.

The octyl radicals here are preferably ethylhexyl radicals, more particularly 2-ethylhexyl radicals and/or the decyl radicals are preferably propylheptyl radicals, more particularly 2-propylheptyl radicals.

A preferred subject of the present invention is a process for producing an ester mixture of the 1,2-, 1,3- or 1,4-esters of cyclohexanedicarboxylic acid, comprising diheptyl cyclohexanedicarboxylate, dinonyl cyclohexanedicarboxylate and heptyl nonyl cyclohexanedicarboxylate by reaction of 1,2-, 1,3- or 1,4-cyclohexanedicarboxylic acid or derivatives thereof which contain no ester groups COOR with a radical R whose alcohol ROH has a higher boiling point at a defined pressure than heptanol at the same pressure, with an amount $(m_1+s_1)$ of heptanol and an amount $m_2$ of nonanol, the reaction mixture being heated at boiling and $m_1$ and $m_2$ corresponding to the mole equivalents of the alcohol radicals of heptanol and nonanol that are to be introduced into the 1,2-, 1,3- or 1,4-cyclohexanedicarboxylic acid or derivatives thereof, $s_1$ being greater than 0 and being more particularly in the range from 0.05 to 0.60 times $(m_1+m_2)$.

The nonyl radicals here are preferably isononyl radicals and/or the heptyl radicals here are preferably isoheptyl radicals.

With particular preference the isononanol used in the above embodiments of the process of the invention as well has an average degree of branching of 1.0 to 2.2 and preferably, moreover, simultaneously comprises less than 25 mol %, more particularly less than 15 mol %, of alcohols having a number of carbon atoms smaller than or greater than 9.

The inventive process preferably does not use any excess amount of $R^2OH$, but instead uses only the amount of $R^2OH$ which corresponds to the amount of alcohol radicals $OR^2$ to be incorporated into $A(COOH)_{x+1}$ or derivatives thereof, more particularly to the amount of alcohol radicals $OR^2$ to be incorporated into $A(COOH)_{x+1}$ or derivates thereof as part of $COOR^2$ ester functions. "No excess amount" means here that preferably less than 0.2 mole equivalent, more preferably less than 0.1 mole equivalent and more particularly less than 0.05 mole equivalent, based on the amount of $R^2OH$ used, is not incorporated as $OR^2$ into $A(COOH)_{x+1}$ or derivatives thereof. With preference, accordingly, at least 0.8 mole equivalent, more preferably at least 0.9 mole equivalent, with further preference at least 0.95 mole equivalent and more particularly at least 0.98 mole equivalent of the alcohol $R^2OH$ used in the process of the invention is introduced as alcohol radical $OR^2$ into $A(COOH)_{x+1}$ or derivative thereof.

The desired composition of the ester mixture under production can be controlled to particularly good effect, and the process product utilized directly, after a lower work-up effort, as plasticizer or plasticizer component, if the components used in the process of the invention, comprising $A(COOH)_{x+1}$ or derivatives thereof and the alcohol mixture of $R^1OH$ and $R^2OH$, comprise less than 50 vol %, preferably less than 35 vol % and more particularly less than 20 vol %, with further preference less than 10 vol %, of components which are not reactants, end products or intermediates in the reaction of $A(COOH)_{x+1}$ or derivates thereof with the alcohols $R^1OH$ and $R^2OH$. These quantity FIGURES do not include the amount $s_1$ of the alcohol $R^1OH$. This amount, however, does include any alcohol which is not $R^1OH$ or $R^2OH$. In order to improve the controllability of the composition of the ester mixture resulting from the process of the invention, the reaction mixture during the reaction comprises preferably less than 0.5 mole equivalent, more preferably less than 0.1 mole equivalent, very preferably less than 0.05 mole equivalent and more particularly less than 0.01 mole equivalent of alcohols which are not alcohols meeting the definition of $R^1OH$ or $R^2OH$, the mole equivalents being based on the entirety of all the alcohols present in the reaction mixture (corresponding to 1 mole equivalent).

The process of the invention produces ester mixtures which comprise preferably at least 5 mol %, more preferably at least 10 mol %, more preferably still at least 15 mol % and more particularly at least 20 mol % of the mixed ester(s) (mol % of the esters $A(COOR^1)(COOR^2)_x$ and $A(COOR^2)(COOR^1)_x$ together), based on the entirety of the esters $A(COOR^1)(COOR^1)_x$, $A(COOR^1)(COOR^2)_x$, $A(COOR^2)(COOR^1)_x$ and $A(COOR^2)(COOR^2)_x$. It may be preferable, moreover, if the entirety of the esters $A(COOR^1)(COOR^1)_x$, $A(COOR^1)(COOR^2)_x$, $A(COOR^2)(COOR^1)_x$ and $A(COOR^2)(COOR^2)_x$ comprises the mixed ester(s) in an amount of at least 25 mol %, with further preference at least 30 mol %, with particular preference at least 35 mol %, more preferably at least 40 mol %, and more particularly at least 45 mol %.

Preference extends to processes whose product comprises not more than 50 mol %, preferably not more than 45 mol % and more particularly not more than 40 mol % of the mixed ester(s) (mol % of the esters $A(COOR^1)(COOR^2)_x$ and $A(COOR^2)(COOR^1)_x$ together), based on the entirety of the esters $A(COOR^1)(COOR^1)_x$, $A(COOR^1)(COOR^2)_x$, $A(COOR^2)(COOR^1)_x$ and $A(COOR^2)(COOR^2)_x$.

In preferred embodiments of the process of the invention, the process facilitates the provision of ester mixtures in which the molar ratio of the esters $A(COOR^1)(COOR^1)_x$, $A(COOR^1)(COOR^2)_x$, $A(COOR^2)(COOR^1)_x$ and $A(COOR^2)(COOR^2)_x$ for x=1 deviates by less than 15 points, preferably by less than 10 points, from the statistically determined expectation value which arises on assumption of complete incorporation of the alcohol radicals $OR^2$, this points value corresponding to the sum total of all amounts of the differences between statistical expectation value and actual molar fraction of each individual ester in the ester mixture in the event that the sum total of the molar fractions of the above-stated esters in the ester mixture adds up to 100.

For x=2, particular preference is given to processes of the invention that provide ester mixtures in which the molar ratio of the esters $A(COOR^1)(COOR^1)_x$, $A(COOR^1)(COOR^2)_x$, $A(COOR^2)(COOR^1)_x$ and $A(COOR^2)(COOR^2)_x$ deviates by less than 25 points, preferably by less than 15 points, more particularly by less than 10 points, from the statistically determined expectation value which arises on assumption of complete incorporation of the alcohol radicals $OR^2$, this points value corresponding to the sum total of all amounts of the differences between statistical expectation value and actual molar fraction of each individual ester in the ester mixture in the event that the sum total of the molar fractions of the above-stated esters in the ester mixture adds up to 100.

The process of the invention is carried out preferably in the presence of a catalyst or of two or more catalysts, with the use as catalyst, for example, of Brønsted or Lewis acids or bases. Having proven themselves as particularly suitable catalysts are sulphuric acid, methanesulphonic acid, p-toluenesulphonic acid, metals or compounds thereof. Examples of particularly preferred metal catalysts are tin powders, tin(II) oxide, tin(II) oxalate, titanic esters such as tetraisopropyl orthotitanate or tetrabutyl orthotitanate, and also zirconium esters such as tetrabutyl zirconate, and also sodium methoxide and potassium methoxide.

The process of the invention can be carried out in typical esterification apparatus known to the skilled person, under customary process conditions. The process takes place preferably at temperatures at or above the boiling point of the alcohol $R^1OH$, the boiling point of water and/or the boiling point of an azeotrope formed from $R^1OH$ and water, allowing the excess amount $s_1$ of the alcohol $R^1OH$ to be removed from the reaction mixture by distillation at the prespecified pressure. A further improvement in the controllability of the composition of the ester mixture resulting from the process of the invention is achieved if the process of the invention is carried out in an apparatus with column. This ensures, preferably, that alcohol $R^2OH$ present in the gas phase during the reaction is recycled as far as possible quantitatively into the reaction vessel. The term "quantitatively" in this context means to an extent of more than 80 mol %, preferably more than 90 mol % and more particularly more than 95 mol %, based on the amount of the alcohol $R^2OH$ used.

The water formed in the reaction is preferably removed from the reaction space. Preferably here the alcohol $R^1OH$ serves as azeotrope former. Optionally in the process of the invention there may be further azeotrope former used, for example cyclohexane, toluene, benzene or xylene.

The time required for implementing the process of the invention can be made shorter if the two alcohols $R^1OH$ and $R^2OH$ are not used concurrently, with at least parts of the alcohol $R^1OH$, instead, being added later than the alcohol $R^2OH$ to $A(COOH)_{x+1}$ or derivatives thereof. Preferably, therefore, at least parts of the alcohol $R^1OH$ are reacted later than the alcohol $R^2OH$ with $A(COOH)_{x+1}$ or derivatives thereof. With preference $A(COOH)_{x+1}$ or derivatives thereof are heated at boiling with the alcohol $R^2OH$ and optionally with a catalyst and also with parts of $R^1OH$, and the remaining parts of the alcohol $R^1OH$ are not added to this reaction mixture until a later point in time.

During the reaction, at regular intervals, it is preferred for GC chromatograms to be prepared or for the acid number to be ascertained in order to observe the progress of the reaction. With preference the reaction is discontinued by cooling and/or destruction of the catalyst, for example by addition of water and/or base, when in the GC chromatograms the residual amount of acid $A(COOH)_{x+1}$ used or of the respective acid derivative used falls below a defined level. Where an acid $A(COOH)_{x+1}$ is used in the process of the invention, the reaction is discontinued preferably when the acid number of the reaction mixture falls below a level of 1.00 mg of KOH per g of reaction mixture, more particularly below a level of 0.50 mg of KOH per g of reaction mixture. The acid number can be determined according to DIN EN ISO 2114. If a derivative of an acid $A(COOH)_{x+1}$, a dimethyl ester, for example, is used in the process of the invention, then the amount of the component used itself or else the amount of an intermediate—for example, in the case of a dimethyl ester used, the amount of all monomethyl esters within the reaction mixture—can be determined, preferably by means of GC, as the limiting point of a reaction which has proceeded substantially to completion. With preference the reaction is discontinued by cooling and/or destruction of the catalyst when the GC chromatograms show a residual amount of acid $A(COOH)_{x+1}$ used or of acid derivative used or of intermediate, such as monomethyl ester, of less than 5.0 area %, more preferably of less than 2.0 area % and more particularly of less than 1.0 area %, based on the total area of all esters in the GC chromatogram.

In one particularly preferred embodiment the process of the invention uses a catalyst which is destroyed when the amount of $R^1OH$ in the reaction mixture has been lowered to less than 15 vol %, preferably less than 10 vol % and more particularly less than 5 vol %, based on the volume of the overall reaction mixture. With particular preference the amount of $R^1OH$ in this case is lowered to less than 3 vol % and more particularly to less than 1 vol %, based on the volume of the overall reaction mixture, preferably by means of distillative removal. In one particularly preferred embodiment of the process of the invention a catalyst is used in the process and in the reaction mixture the amount of $R^1OH$ has been lowered to less than 20 mol %, preferably to less than 15 mol %, more preferably to less than 10 mol % and more particularly to less than 5 mol %, based on the excess amount $s_1$ of the alcohol $R^1OH$, before the catalyst is destroyed. The destruction of the catalyst takes place preferably here when reaction monitoring has found a reaction progress of at least 90%—for example, by the finding, in the GC chromatograms monitoring the reaction progress, of a residual amount of acid $A(COOH)_{x+1}$ used or of acid derivative used or of intermediate, such as monomethyl ester, for example, of less than 5.0 area %, more particularly of less than 1.0 area %, based on the total area of all esters in the GC chromatogram, or by the acid number falling below a defined level. The lowering of the amount of $R^1OH$ achieves improved controllability of the process of the invention to give ester mixtures whose compositions exhibit particularly small deviations from the statistical expectation value.

After the end of the reaction, the reaction mixture is worked up in a conventional way.

A preferred subject of the present invention is a process for producing ester mixtures comprising $A(COOR^1)(COOR^1)_x$, $A(COOR^1)(COOR^2)_x$, $A(COOR^2)(COOR^1)_x$ and $A(COOR^2)(COOR^2)_x$ by reaction of $A(COOH)_{x+1}$ or derivatives thereof, which contain no ester groups COOR having a radical R whose alcohol ROH has a higher boiling point at a defined pressure than the alcohol $R^1OH$ of the radical $R^1$ at the same pressure, with an amount $(m_1+s_1)$ of $R^1OH$ and an amount $m_2$ of $R^2OH$, in which
the reaction mixture is heated at boiling,
the reaction is discontinued preferably when a reaction progress of at least 90% has been found, for example by the acid number of the reaction mixture falling below a level of 1.00 mg of KOH per g of reaction mixture, more particularly a level of 0.50 mg of KOH per g of reaction mixture, or by the finding, in the GC chromatograms monitoring reaction progress, of a residual amount of a component converted during the reaction, such as the acid $A(COOH)_{x+1}$ or derivative thereof, or of an intermediate, of less than 5.0 area %, more particularly of less than 1.0 area %, based on the total area of all esters in the GC chromatogram,
preferably at least 0.8 mole equivalent, more particularly at least 0.9 mole equivalent and more particularly at least 0.95 mole equivalent of the alcohol $R^2OH$ used in the process of the invention is introduced as alcohol radical $OR^2$ into $A(COOH)_{x+1}$ or derivative thereof,
preferably a catalyst is used and in the reaction mixture the amount of $R^1OH$ has been lowered to less than 20 mol %, preferably to less than 15 mol %, more preferably to less than 10 mol % and more particularly to less than 5 mol %, based on the excess amount $s_1$ of the alcohol $R^1OH$, before the catalyst is destroyed, and where
A is an aromatic, alicyclic or aliphatic radical,
x is 1 or 2,
$R^1$ and $R^2$ independently of one another are substituted or unsubstituted aryl radicals or linear or branched, substituted or unsubstituted alkyl radicals having 3 to 20 carbon atoms, the alcohol $R^1OH$ having a lower boiling point at a defined pressure than the alcohol $R^2OH$ at the same pressure,
$m_1$ and $m_2$ correspond to the mole equivalents of the alcohol radicals $OR^1$ and $OR^2$ to be introduced into $A(COOH)_{x+1}$ or derivatives thereof, and
$s_1$ is greater than 0 and more particularly is in the range from 0.05 to 0.60 times $(m_1+m_2)$.

In this case, preferably, the molar ratio of the esters $A(COOR^1)(COOR^1)_x$, $A(COOR^1)(COOR^2)_x$, $A(COOR^2)(COOR^1)_x$ and $A(COOR^2)(COOR^2)_x$ for x=1 deviates by less than 15 points, preferably by less than 10 points, from the statistically determined expectation value which arises on assumption of complete incorporation of the alcohol radicals $OR^2$, this points value corresponding to the sum total of all amounts of the differences between statistical expectation value and actual molar fraction of each individual ester in the ester mixture in the event that the sum total of the molar fractions of the abovementioned esters in the ester mixture adds up to 100.

In this case, preferably, for x=2 the molar ratio of the esters $A(COOR^1)(COOR^1)_x$, $A(COOR^1)(COOR^2)_x$, $A(COOR^2)(COOR^1)_x$ and $A(COOR^2)(COOR^2)_x$ deviates by less than 25 points, preferably by less than 15 points, more particularly by less than 10 points from the statistically determined expectation value which arises on assumption of complete incorporation of the alcohol radicals $OR^2$, this points value corresponding to the sum total of all amounts of the differences between statistical expectation value and actual molar fraction of each individual ester in the ester mixture in the event that the sum total of the molar fractions of the abovementioned esters in the ester mixture adds up to 100.

In certain embodiments of the process of the invention, an ester mixture is produced in which the esters have hydrogenable functionalities such as, for example, C=C double bonds or aromatic radicals. These functionalities, optionally after one or more work-up steps may be hydrogenated in a subsequent process step and the esters may be converted accordingly into saturated compounds (that is, compounds free from aromatics or from multiple C—C bonding) which are preferentially suitable for use as plasticizers or a plasticizer component in polymers, for example PVC. The ester mixture in the process of the invention is preferably a mixture of phthalic acid, of terephthalic acid or of isophthalic acid, and in a subsequent process step the ester mixture is preferably hydrogenated.

A further preferred subject of the present invention is a process for producing ester mixtures comprising 1,2-, 1,3- or 1,4-esters of cyclohexanedicarboxylic acid comprising dipentyl cyclohexanedicarboxylate, diisononyl cyclohexanedicarboxylate and pentyl isononyl cyclohexanedicarboxylate, by reaction of terephthalic acid, isophthalic acid or phthalic acid or derivatives of these acids which contain no ester groups COOR with a radical R whose alcohol ROH has a higher boiling point at a defined pressure than pentanol at the same pressure,
with an amount $(m_1+s_1)$ of pentanol and an amount $m_2$ of isononanol,
where the reaction mixture is heated at boiling and a catalyst is used and in the reaction mixture the amount of pentanol has been lowered to less than 20 mol %, preferably to less than 15 mol %, more preferably to less than 10 mol % and more particularly to less than 5 mol %, based on the excess amount $s_1$ of the alcohol $R^1OH$, before the catalyst is destroyed, the ester mixture is subjected to ring hydrogenation in a subsequent process step, and where $m_1$ and $m_2$ correspond to the mole equivalents of the alcohol radicals of pentanol and isononanol that are to be introduced into terephthalic acid or derivatives thereof and $s_1$ is greater than 0 and more particularly is in the range from 0.05 to 0.60 times $(m_1+m_2)$.

Another preferred subject of the present invention is a process for producing ester mixtures comprising 1,2-, 1,3- or 1,4-esters of cyclohexanedicarboxylic acid comprising dipentyl cyclohexanedicarboxylate, dipropylheptyl cyclohexanedicarboxylate and pentyl propylheptyl cyclohexanedicarboxylate, by reaction of terephthalic acid, isophthalic acid or phthalic acid or derivatives of these acids which contain no ester groups COOR with a radical R whose alcohol ROH has a higher boiling point at a defined pressure than pentanol at the same pressure, with an amount $(m_1+s_1)$ of pentanol and an amount $m_2$ of propylheptanol, where the reaction mixture is heated at boiling and a catalyst is used and in the reaction mixture the amount of $R^1OH$ has been lowered to less than 20 mol %, preferably to less than 15 mol %, more preferably to less than 10 mol % and more particularly to less than 5 mol %, based on the excess amount $s_1$ of the alcohol pentanol, before the catalyst is destroyed, the ester mixture is subjected to ring hydrogenation in a subsequent process step, and where $m_1$ and $m_2$ correspond to the mole equivalents of the alcohol radicals of pentanol and propylheptanol that are to be introduced into terephthalic acid or derivatives thereof and $s_1$ is greater than 0 and more particularly is in the range from 0.05 to 0.60 times $(m_1+m_2)$.

In the case of the two above embodiments, in turn, the pentyl and isononyl radicals present are preferably those as defined earlier on above in the text.

A further preferred subject of the present invention is a process for producing ester mixtures comprising 1,2-, 1,3- or 1,4-esters of cyclohexanedicarboxylic acid comprising diisoheptyl cyclohexanedicarboxylate, isononyl cyclohexanedicarboxylate and isoheptylisononyl cyclohexanedicarboxylate, by reaction of terephthalic acid, isophthalic acid or phthalic acid or derivatives of these acids which contain no ester groups COOR with a radical R whose alcohol ROH has a higher boiling point at a defined pressure than isoheptanol at the same pressure, with an amount $(m_1+s_1)$ of isoheptanol and amount $m_2$ of isononanol, where the reaction mixture is heated at boiling and a catalyst is used and in the reaction mixture the amount of $R^1OH$ has been lowered to less than 20 mol %, preferably to less than 15 mol %, more preferably to less than 10 mol % and more particularly to less than 5 mol %, based on the excess amount $s_1$ of the alcohol isoheptanol, before the catalyst is destroyed, the ester mixture is subjected to ring hydrogenation in a subsequent process step, and where $m_1$ and $m_2$ correspond to the mole equivalents of the alcohol radicals of isoheptanol and isononanol that are to be introduced into terephthalic acid or derivatives thereof and $s_1$ is greater than 0 and more particularly is in the range from 0.05 to 0.60 times $(m_1+m_2)$.

A further subject of the present invention is an ester mixture produced by the process of the invention described.

More particularly a subject of the present invention is an ester mixture which has been produced by any of the above-described processes of the invention, and in which the molar ratio of the esters $A(COOR^1)(COOR^1)_x$, $A(COOR^1)(COOR^2)_x$, $A(COOR^2)(COOR^1)_x$ and $A(COOR^2)(COOR^2)_x$ for $x=1$ deviates by less than 15 points, preferably by less than 10 points, from the statistically determined expectation value which arises on assumption of complete incorporation of the alcohol radicals $OR^2$, this points value corresponding to the sum total of all amounts of the differences between statistical expectation value and actual molar fraction of each individual ester in the ester mixture in the event that the sum total of the molar fractions of the abovementioned esters in the ester mixture adds up to 100.

A further subject of the present invention is an ester mixture which has been produced by any of the above-described processes of the invention, in which the molar ratio of the esters $A(COOR^1)(COOR^1)_x$, $A(COOR^1)(COOR^2)_x$, $A(COOR^2)(COOR^1)_x$ and $A(COOR^2)(COOR^2)_x$ for $x=2$ deviates by less than 25 points, preferably by less than 15 points, more particularly by less than 1 point from the statistically determined expectation value which arises on assumption of complete incorporation of the alcohol radicals $OR^2$, this points value corresponding to the sum total of all amounts of the differences between statistical expectation value and actual molar fraction of each individual ester in the ester mixture in the event that the sum total of the molar fractions of the abovementioned esters in the ester mixture adds up to 100.

A subject of the present invention, moreover, is the use of the process of the invention for adjusting processing-relevant and/or application-relevant properties of an ester mixture by controlling the quantitative distribution of the esters in the ester mixture. Examples of the influencing of a number of processing-relevant and application-relevant properties in the area of plasticizers through the choice of the $m_1:m_2$ ratio have been given above in the text.

Figure 1:
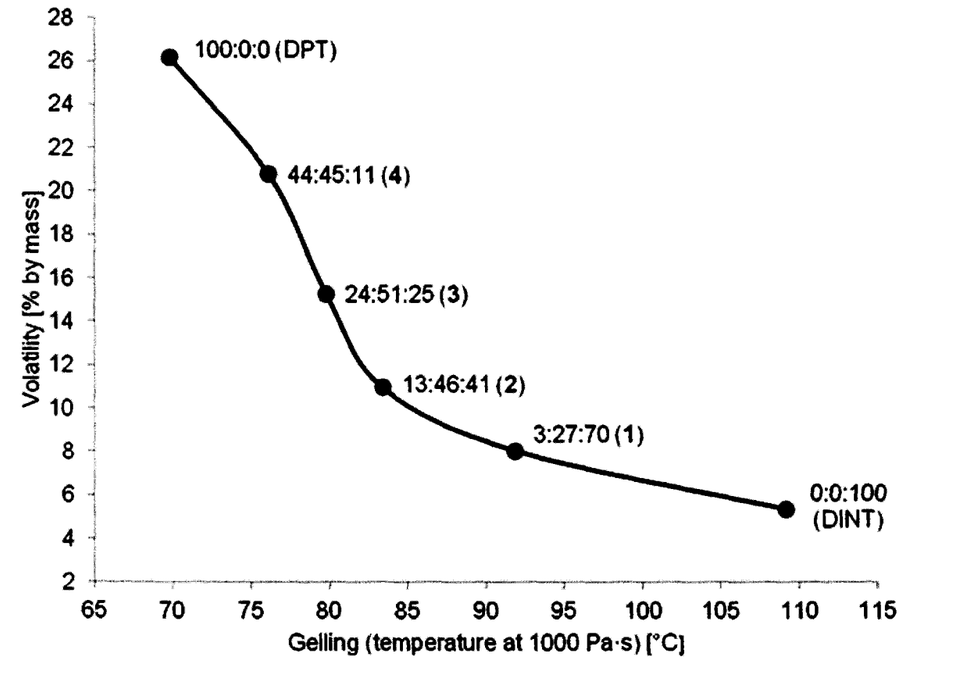
The FIGURE shows a plot of gelling temperature against volatility for the ester mixtures of various compositions, diisopentyl terephthalate (DPT) and diisononyl terephthalate (DINT) (the associated molar ratio of diisopentyl terephthalate:isopentyl isononyl terephthalate:diisononyl terephthalate in the respective ester mixture is reported at the data points)

A particularly preferred subject of the present invention is the use of the process of the invention for controlling the gelling temperature of a plastisol comprising ester mixture and/or for controlling the volatility of a test specimen comprising ester mixture, through control of the quantitative distribution of the esters in the ester mixture. Plotted in the FIGURE for ester mixtures of the invention with different quantitative distributions of the esters present is the gelling temperature of the plastisols against the associated volatility of the films comprising the same ester mixture. From this FIGURE it is apparent that products (plastisols or films) with different mixtures according to the invention have volatilities and gelling temperatures that deviate from one another, and that the skilled person is able to select the appropriate composition of an ester mixture according to the volatility and gelling temperature that are needed for processing and/or application. The same applies to other properties such as, for example, the compatibility of the ester mixtures with polymers, which is determinable by methods including the test described in the Experimental section; the Shore hardness, which describes the plasticizer efficiency; the change in the viscosity of a corresponding plastisol after storage; or the change in mass of a corresponding plastisol on water storage. The process of the invention, then, enables the skilled person to produce ester mixtures having the desired properties in a targeted way, since the quantitative distribution of the esters in the ester mixture can be adjusted in a targeted way by means of the process of the invention.

The ester mixture produced by means of the process of the invention is used preferably as a plasticizer or as a component of a mixture of two or more polymer-plasticizing compounds, likewise referred to here as a plasticizer mixture.

A further subject of the present invention is the use of an ester mixture produced by the process of the invention as a plasticizer for polymers.

Suitable polymers are preferably selected from the group consisting of polyvinyl chloride (PVC), homo- or copolymers based on ethylene, propylene, butadiene, vinyl acetate, glycidyl acrylate, glycidyl methacrylate, ethyl acrylate, butyl acrylate or methacrylate with alkoxy radicals of branched or unbranched alcohols having one to ten carbon atoms, acrylonitrile or cyclic olefins, polyvinylidene chloride (PVDC), polyacrylates, more particularly polymethyl methacrylate (PMMA), polyalkyl methacrylate (PAMA), polyureas, silylated polymers, fluoropolymers, especially polyvinylidene fluoride (PVDF), polytetrafluoroethylene (PTFE), polyvinyl acetate (PVAc), polyvinyl alcohol (PVA), polyvinyl acetals, especially polyvinyl butyral (PVB), polystyrene polymers, especially polystyrene (PS), expandable polystyrene (EPS), acrylonitrile-styrene-acrylate (ASA), styrene-acrylonitrile (SAN), acrylonitrile-butadiene-styrene (ABS), styrene-maleic anhydride copolymer (SMA), styrene-methacrylic acid copolymer, polyolefins, especially polyethylene (PE) or polypropylene (PP), thermoplastic polyolefins (TPO), polyethylene-vinyl acetate (EVA), polycarbonates, polyethylene terephthalate (PET), polybutylene terephthalate (PBT), polyoxymethylene (POM), polyamide (PA), polyethylene glycol (PEG), polyurethane (PU), thermoplastic polyurethane (TPU), polysulphides (PSu), biopolymers, especially polylactic acid (PLA), polyhydroxybutyral (PHB), polyhydroxyvaleric acid (PHV), polyesters, starch, cellulose and cellulose derivatives, especially nitrocellulose (NC), ethylcellulose (EC), cellulose acetate (CA), cellulose acetate/butyrate (CAB), rubber and silicones.

Preferred polymers are polyvinyl chloride, copolymers of vinyl chloride with vinyl acetate or with butyl acrylate, polyalkyl methacrylate (PAMA), polyvinyl butyral (PVB), polyurethane, polysulphides, polylactic acid (PLA), polyhydroxybutyral (PHB) and nitrocellulose.

Particularly preferred is the use of an ester mixture produced by the process of the invention as a plasticizer for PVC.

The ester mixture produced by means of the process of the invention is used preferably as a plasticizer in adhesives, sealants, coating materials, paints, inks, plastisols, foams, synthetic leather, floorcoverings (e.g. top layer), roofing membranes, underbody protection, fabric coatings, cables, wire insulation, hoses, extruded articles, films, in the automotive interior area, in wallcoverings, liquid inks, toys, contact films, food packaging or medical articles, for example tubes or blood bags.

A further subject of the present invention is a composition comprising an ester mixture which has been produced by the process of the invention, and also one or more polymers from the group consisting of polyvinyl chloride, copolymers of vinyl chloride with vinyl acetate or with butyl acrylate, polyalkyl methacrylate (PAMA), polyvinyl butyral (PVB), polyurethane, polysulphides, polylactic acid (PLA), polyhydroxybutyral (PHB) and nitrocellulose.

Based on 100 parts by mass of polymer, preferred compositions comprise from 5 to 200, preferably from 10 to 150, parts by mass of plasticizer.

Preference is given to using the ester mixture of the invention as a plasticizer for polyvinyl chloride, and particular preference is given, accordingly, to compositions comprising the ester mixture of the invention and PVC.

The polymer is preferably a suspension-, bulk-, microsuspension- or emulsion-PVC.

Preferred compositions of the invention may comprise the ester mixture of the invention and also at least one further polymer-plasticizing compound, i.e. a further plasticizer. In one particularly preferred embodiment of the composition of the invention it comprises less than 5% by mass and more particularly less than 0.5% by mass of phthalate-containing compounds. The further plasticizers are preferably selected from the group of the adipates, benzoates, for example monobenzoates or glycol dibenzoates, chlorinated hydrocarbons, citrates, cyclohexanedicarboxylates, epoxidized fatty acid esters, epoxidized vegetable oils, epoxidized acylated glycerides, furandicarboxylates, phosphates, phthalates (preferably in very small amounts), succinates, sulphonamides, sulphonates, terephthalates, trimellitates or oligomeric or polymeric esters based on adipic, succinic or sebacic acid. Particularly preferred are alkyl benzoates, dialkyl adipates, glycerol esters, trialkyl citrates, acylated trialkyl citrates, trialkyl trimellitates, glycol dibenzoates, dialkyl terephthalates, esters of furandicarboxylic acid, dialkanoyl esters of dianhydrohexitols (e.g. isosorbitol) and dialkyl esters of 1,2-, 1,3- or 1,4-cyclohexanedicarboxylic acid.

In one embodiment the composition of the invention comprises the ester mixture of the invention and also less than 20% by mass of, less than 10% by mass of or no further plasticizers, the % by mass being based on the total mass of the composition.

Compositions of the invention preferably comprise, in addition to the polymer or to a mixture of two or more polymers and the ester mixture of the invention, one or more additives from the group of heat stabilizers, fillers, pigments, blowing agents, biocides, UV stabilizers, light stabilizers, costabilizers, antioxidants, viscosity regulators, deaerating agents, adhesion promoters, lubricants and colorants.

The compositions of the invention can be used in adhesives, sealants, coating materials, paints, inks, plastisols, foams, synthetic leather, floorcoverings (e.g. top layer), roofing membranes, underbody protection, fabric coatings, cables, wire insulation, hoses, extruded articles, films, in the automotive interior area, in wallcoverings, liquid inks, toys, contact films, food packaging or medical articles, for example tubes or blood bags.

Having generally described this invention, a further understanding can be obtained by reference to certain specific examples which are provided herein for purposes of illustration only, and are not intended to be limiting unless otherwise specified.

Experimental Section:

Boiling Range of the Alcohols:

The alcohols used in the examples or used for synthesizing the esters used in the examples had the following boiling ranges:

Isononanol (Evonik Industries AG, purity>99%): 205 to 215° C. at 1013 hPa;

Isopentanol (mixture of n-pentanol (Sigma Aldrich, purity>99%) and 2-methylbutanol (Sigma Aldrich, purity>99%) in a molar ratio of 1:1): 129 to 138° C. at 1013 hPa Acid Number:

The acid number was determined in accordance with DIN EN ISO 2114.

GC Analyses:

The GC analysis took place with the following parameters:

Capillary column: 30 m DB5; 0.25 mm ID; 0.25 µm film
Carrier gas: helium
Column head pressure: 80 kPa
Split: about 23.8 ml/min
Oven temperature programme (duration: 51 min): 50° C. (for 1 min), heating at 7.5° C./min to 350° C. (hold temperature for 1 min)
Injector: 350° C.
Detector (FID): 400° C.
Injection volume: 1.0 µl The components in the sample chromatogram were identified using a comparative solution of the relevant esters. The signals in the sample chromatogram were subsequently standardized to 100 area %. The amount-of-substance ratios were determined in sufficient approximation from the area ratios of the individual signals. The purity was determined via the fraction of the product signals as a portion of the total areas in the chromatogram.

Diisononyl terephthalate (DINT) and diisopentyl terephthalate (DPT) were produced, as known in the related art, by esterification of dimethyl terephthalate with the above-indicated alcohols isononanol and isopentanol, respectively.

Example 1 (Inventive)

Transesterification of dimethyl terephthalate with isopentanol and isononanol (1.0:18.5:80.5)

A transesterification apparatus comprising stirring flask with stirrer, immersion tube, thermometer and 20 cm Raschig ring column with top-mounted distillation head was charged with dimethyl terephthalate (Sigma Aldrich, purity >99%) ($m_b$) and with the alcohols $R^1OH$ ($m_1+s_1$) and $R^2OH$ ($m_2$). The apparatus was flushed with nitrogen (6 l/h) for at least one hour via the immersion tube. Subsequently 0.25 wt % of tetra-n-butyl titanate (Sigma Aldrich, purity >97%) was added, based on the mass of terephthalic ester. The mixture was subsequently heated at boiling and low-boiling components were removed by distillation. In the event of a sharp increase in the overhead temperature, the distillation was interrupted by closure of the drain tap, and the reaction was left at reflux until a stable boiling temperature was established. During the reaction, the liquid phase temperature rose from $T^1$ to $T^2$. GC chromatograms were prepared hourly during the reaction. As soon as these chromatograms indicated a residual amount of monomethyl ester of less than 0.5 area %, based on the total area of all esters in the GC chromatogram, the remaining volatile components of the reaction mixture were distilled off under reduced pressure (about 1 mbar) at a liquid phase temperature of $T^3$, and so the residual amount of the alcohol $R_1OH$ (by GC) was less than 5 mol %, based on the excess amount $s_1$ of the alcohol $R_1OH$. With the heating shut off, the contents of the flask were subsequently cooled to about 80° C. by admission of nitrogen at 20 mbar. The acid number of the flask contents was determined. According to the result, the reaction medium was neutralized by slow dropwise addition of three times the stoichiometric amount of base (10% strength aqueous NaOH solution) and stirred for 15 minutes with introduction of nitrogen (6 l/h) at 80° C. The batch was subsequently evacuated slowly from the ambient pressure to about 1 mbar, at which point it was heated to about 120° C. and residual volatiles were removed by means of nitrogen introduction at constant temperature. The nitrogen flow rate is set such that the pressure did not exceed 20 mbar. When the residual alcohol content according to GC analysis was less than 0.025 area %, the heating was shut off and cooling took place to 80° C. under reduced pressure and with introduction of nitrogen. At this temperature, the product was filtered on a Büchner funnel with filter paper and precompacted filter cake of filter aid (D14 Perlite) into a suction bottle by reduced pressure. A GC analysis was carried out on the filtrate, and used for analysis of the purity (R) and the composition of the product.

TABLE 2

| values measured and calculated for Example 1 | |
|---|---|
| $R^1OH$ = isopentanol | $m_1 + s_1$ = 308.5 g |
| Amount of $R^1OH$ = amount of $R^1$ equivalents ($C_5$) | 3.5 mol |
| $R^2OH$ = isononanol | $m_2$ = 1296 g |
| Amount of $R^2OH$ = amount of $R^2$ equivalents ($C_9$) | 9 mol |
| Dimethyl terephthalate | $m_b$ = 970 g |
| Amount | 5 mol |
| → Amount of ester functions | 10 mol |
| Expected molar fraction of the $R^1$ functions as a proportion of $R^1$ and $R^2$-functions in the ester mixture (on full incorporation of $R^2$) | 10 mol − 9 mol = 1 mol corresponding to 10 mol % |
| Ratio $m_1$:$m_2$ | 0.1:0.9 |
| $s_1$ | 3.5 mol − (10.0 mol − 9.0 mol) = 2.5 mol |
| $T^1 \to T^2$ (liquid phase temperature start → end) | 131° C. → 200° C. |
| $T^3$ | 200° C. |
| R (purity) | >99.9% |
| Statistical expectation values for complete incorporation of $C_9$: ($C_5/C_5$):($C_5/C_9$):($C_9/C_9$) | 1.0:18.0:81.0 (expected $C_5$ fraction: 10%) |
| Composition according to GC ($C_5/C_5$):($C_5/C_9$):($C_9/C_9$) | 1.0:18.5:80.5 ($C_5$-fraction: 10.3%) Deviation: \|1 − 1\| + \|18.5 − 18.0\| + \|80.5 − 81.0\| = 1 |

This gave 1902 g of worked-up ester mixture.

Example 2 (Inventive)

Transesterification of dimethyl terephthalate with isopentanol and isononanol (0:12:87)

Example 2 was carried out as described for Example 1.

TABLE 3

| values measured and calculated for Example 2 | |
|---|---|
| $R^1OH$ = isopentanol | $m_1 + s_1$ = 264.5 g |
| Amount of $R^1OH$ = amount of $R^1$ equivalents ($C_5$) | 3 mol |
| $R^2OH$ = isononanol | $m_2$ = 1368 g |
| Amount of $R^2OH$ = amount of $R^2$ equivalents ($C_9$) | 9.5 mol |
| Dimethyl terephthalate | $m_b$ = 970 g |
| Amount | 5 mol |
| → Amount of ester functions | 10 mol |

TABLE 3-continued

| values measured and calculated for Example 2 | |
|---|---|
| Expected molar fraction of the $R^1$ functions as a proportion of $R^1$ and $R^2$ functions in the ester mixture (on full incorporation of $R^2$) | 10 mol − 9.5 mol = 0.5 mol corresponding to 5 mol % |
| Ratio $m_1:m_2$ | 0.05:0.95 |
| $s_1$ | 3 mol − (10 mol − 9.5 mol) = 2.5 mol |
| $T^1 \rightarrow T^2$ (liquid phase temperature start → end) | 138° C. → 200° C. |
| $T^3$ | 200° C. |
| R (purity) | 99.7% |
| Statistical expectation values for complete incorporation of $C_9$: $(C_5/C_5):(C_5/C_9):(C_9/C_9)$ | 0.25:9.5:90.25 (expected $C_5$ fraction: 5.0%) |
| Composition according to GC $(C_5/C_5):(C_5/C_9):(C_9/C_9)$ | 0.4:12.4:87.2 ($C_5$ fraction: 6.6%) Deviation: \|0.4 − 0.25\| + \|12.4 − 9.5\| + \|87.2 − 90.25\| = 6.1 |

This gave 1966 g of worked-up ester mixture.

Example 3 (Inventive)

Transesterification of dimethyl terephthalate with isopentanol and isononanol (13:46:41)

Example 3 was carried out as described for Example 1.

TABLE 4

| values measured and calculated for Example 3 | |
|---|---|
| $R^1OH$ = isopentanol Amount of $R^1OH$ = amount of $R^1$ equivalents ($C_5$) | $m_1 + s_1$ = 441 g 5 mol |
| $R^2OH$ = isononanol Amount of $R^2OH$ = amount of $R^2$ equivalents ($C_9$) | $m_2$ = 720 g 5 mol |
| Dimethyl terephthalate Amount → Amount of ester functions | $m_b$ = 776 g 4 mol 8 mol |
| Expected molar fraction of $R^1$ functions as a proportion of $R^1$ and $R^2$ functions in the ester mixture (on full incorporation of $R^2$) | 8 mol − 5 mol = 3 mol corresponding to 37.5 mol % |
| Ratio $m_1:m_2$ | 3:5 corresponding to 0.375:0.625 |
| $s_1$ | 5 mol − (8 mol − 5 mol) = 2 mol |
| $T^1 \rightarrow T^2$ (liquid phase temperature start → end) | 139° C. → 215° C. |
| $T^3$ | 190° C. |
| R (purity) | 99.7% |
| Statistical expectation values for complete incorporation of $C_9$: $(C_5/C_5):(C_5/C_9):(C_9/C_9)$ | 14.1:46.8:39.1 (expected $C_5$ fraction: 37.5%) |
| Composition according to GC $(C_5/C_5):(C_5/C_9):(C_9/C_9)$ | 13.4:45.8:40.8 ($C_5$-fraction: 36%) Deviation: \|14.1 − 13.4\| + \|46.8 − 45.8\| + \|39.1 − 40.8\| = 3.4 |

This gave 1270 g of worked-up ester mixture 13:46:41.

Example 4 (Inventive)

Transesterification of dimethyl terephthalate with isopentanol and isononanol (24:51:25)

Example 4 was carried out as described for Example 1.

TABLE 5

| values measured and calculated for Example 4 | |
|---|---|
| $R^1OH$ = isopentanol Amount of $R^1OH$ = amount of $R^1$ equivalents ($C_5$) | $m_1 + s_1$ = 705 g 8 mol |
| $R^2OH$ = isononanol Amount of $R^2OH$ = amount of $R^2$ equivalents ($C_9$) | $m_2$ = 576 g 4 mol |
| Dimethyl terephthalate Amount → Amount of ester functions | $m_b$ = 776 g 4 mol 8 mol |
| Expected molar fraction of $R^1$ functions as a proportion of $R^1$ and $R^2$ functions in the ester mixture (on full incorporation of $R^2$) | 8 mol − 4 mol = 4 mol corresponding to 50 mol % |
| Ratio $m_1:m_2$ | 0.5:0.5 |
| $s_1$ | 8 mol − (8 mol − 4 mol) = 4 mol |
| $T^1 \rightarrow T^2$ (liquid phase temperature start → end) | 123° C. → 174° C. |
| $T^3$ | 180° C. |
| R (purity) | 99.9% |
| Statistical expectation values for complete incorporation of $C_9$: $(C_5/C_5):(C_5/C_9):(C_9/C_9)$ | 25.0:50.0:25.0 (expected $C_5$ fraction: 50%) |
| Composition according to GC $(C_5/C_5):(C_5/C_9):(C_9/C_9)$ | 24.0:50.5:25.5 ($C_5$ fraction: 49.5%) Deviation: \|25.0 − 24.0\| + \|50.0 − 50.5\| + \|25 − 25.5\| = 2 |

This gave 1254 g of worked-up ester mixture 24:51:25.

Example 5 (Inventive)

Transesterification of dimethyl terephthalate with butanol and 2-ethylhexanol (3:27:70)

Example 5 was carried out as described for Example 1.

TABLE 6

| values measured and calculated for Example 5 | |
|---|---|
| $R^1OH$ = n-butanol (Sigma Aldrich, purity ≥99.4%) Amount of $R^1OH$ = amount of $R^1$ equivalents ($C_5$) | $m_1 + s_1$ = 154 g 2.1 mol |
| $R^2OH$ = 2-ethylhexanol (Sigma Aldrich, purity ≥99%) Amount of $R^2OH$ = amount of $R^2$ equivalents ($C_9$) | $m_2$ = 543 g 4.2 mol |
| Dimethyl terephthalate Amount → Amount of ester functions | $m_b$ = 485 g 2.5 mol 5 mol |
| Expected molar fraction of $R^1$ functions as a proportion of $R^1$ and $R^2$ functions in the ester mixture (on full incorporation of $R^2$) | 5 mol − 4.2 mol = 0.8 mol corresponding to 16 mol % |
| Ratio $m_1:m_2$ | 0.8:4.2 corresponding to 0.16:0.84 |
| $s_1$ | 2.1 mol − (5 mol − 4.2 mol) = 1.3 mol |
| $T^1 \rightarrow T^2$ (liquid phase temperature start → end) | 123° C. → 215° C. |
| $T^3$ | 160° C. |
| R (purity) | >99.9% |
| Statistical expectation values for complete incorporation of $C_9$: $(C_4/C_4):(C_4/C_8):(C_8/C_8)$ | 2.6:26.9:70.5 (expected $C_4$ fraction: 16%) |

TABLE 6-continued values measured and calculated for Example 5

| | |
|---|---|
| Composition according to GC ($C_4/C_4$):($C_4/C_8$):($C_8/C_8$) | 2.5:27.3:70.2 ($C_4$ fraction: 16%) |
| | Deviation: |
| | \|2.5 − 2.6\| + \|27.3 − 26.9\| + \|70.2 − 70.5\| = 0.8 |

This gave 920 g of worked-up ester mixture.

Example 6 (Inventive)

Transesterification of dimethyl terephthalate with butanol and 2-ethylhexanol (11:45:44)

Example 6 was carried out as described for Example 1.

TABLE 7 values measured and calculated for Example 6

| | |
|---|---|
| $R^1OH$ = n-butanol (Sigma Aldrich, purity ≥99.4%) Amount of $R^1OH$ = amount of $R^1$ equivalents ($C_5$) | $m_1 + s_1$ = 232 g 3.1 mol |
| $R^2OH$ = 2-ethylhexanol (Sigma Aldrich, purity ≥99%) Amount of $R^2OH$ = amount of $R^2$ equivalents ($C_9$) | $m_2$ = 407 g 3.1 mol |
| Dimethyl terephthalate Amount → Amount of ester functions | $m_b$ = 485 g 2.5 mol 5 mol |
| Expected molar fraction of $R^1$ functions as a proportion of $R^1$ and $R^2$ functions in the ester mixture (on full incorporation of $R^2$) | 5 mol − 3.1 mol = 1.9 mol corresponding to 38 mol % |
| Ratio $m_1$:$m_2$ | 1.9:3.1 corresponding to 0.38:0.62 |
| $s_1$ | 3.1 mol − (5 mol − 3.1 mol) = 1.2 mol |
| $T^1 \to T^2$ (liquid phase temperature start → end) | 123° C. → 200° C. |
| $T^3$ | 160° C. |
| R (purity) | 99.6% |
| Statistical expectation values for complete incorporation of $C_9$: ($C_4/C_4$):($C_4/C_8$):($C_8/C_8$) | 14.4:47.1:38.5 (expected $C_4$ fraction: 38%) |
| Composition according to GC ($C_4/C_4$):($C_4/C_8$):($C_8/C_8$) Deviation: | 10.8:45.0:44.1 ($C_4$ fraction: 33%) |
| | \|14.4 − 10.8\| + \|45.0 − 47.1\| + \|44.1 − 38.5\| = 11.3 |

This gave 850 g of worked-up ester mixture.

Example 7 (Inventive)

Transesterification of dimethyl terephthalate with isopentanol and isononanol (44:45:11)

A transesterification apparatus comprising stirring flask with stirrer, immersion tube, thermometer and 20 cm Raschig ring column with top-mounted distillation head was charged with dimethyl terephthalate (Sigma Aldrich, purity>99%) ($m_b$) and this initial charge was suspended in the alcohol $R^2OH$ ($m_2$). The apparatus was flushed with nitrogen (6 l/h) for at least one hour via the immersion tube. Subsequently 0.25 wt % of tetra-n-butyl titanate (Sigma Aldrich, purity>97%) was added, based on the mass of the terephthalic ester. To homogenize the reaction mixture, 300 ml of the alcohol $R^1OH$ were added. The reaction mixture was subsequently heated slowly with stirring. Reaction onset was at liquid phase temperature $T^1$ and overhead temperature 62° C. From this point, methanol was produced, and was removed continuously under gentle reflux via the distillation head from the reaction. In the event of a sharp increase in the overhead temperature, the distillation was interrupted by closure of the drain tap, and the reaction was left at reflux until a stable boiling temperature was established. As soon as distillate was no longer produced in spite of the raising of the liquid phase temperature, the residual amount ($m_1+s_1$−300 ml) of alcohol $R^1OH$ was added at a rate of addition such that the liquid phase temperature did not fall below 150° C. The reaction was subsequently heated continuously along the boiling temperature of the mixture up to $T^2$, allowing the production of a continual distillate. Again, on a sudden increase in the overhead temperature, the distillation was interrupted by closure of the discharge tap, and the reaction was left at reflux until a stable boiling temperature was established. As soon as no further distillate was obtained in spite of the raising of the liquid phase temperature, and GC analysis found a residual amount of monomethyl ester of less than 0.5 area %, based on the total area of all esters, the remaining volatile components were distilled off directly at $T^3$ by application of reduced pressure, and so the residual amount of the alcohol $R^1OH$ was below 5 mol %, based on the excess amount $s_1$ of the alcohol $R^1OH$ (according to GC). With the heating shut off, the contents of the flask were subsequently cooled to about 80° C. by admission of nitrogen. The acid number of the flask contents was determined. According to the result, the reaction medium was neutralized by slow dropwise addition of three times the stoichiometric amount of base (10% strength aqueous NaOH solution) and stirred for 15 minutes with introduction of nitrogen (6 l/h) at 80° C. The batch was subsequently evacuated slowly from the ambient pressure to about 1 mbar, at which point it was heated to about 120° C. and residual volatiles were removed by means of nitrogen introduction at constant temperature. The nitrogen flow rate was set such that the pressure did not exceed 20 mbar. When the residual alcohol content according to GC analysis was less than 0.025 area %, the heating was shut off and cooling took place to 80° C. under reduced pressure and with introduction of nitrogen. At this temperature, the product was filtered on a Buchner funnel with filter paper and precompacted filter cake of filter aid (D14 Perlite) into a suction bottle by reduced pressure. A GC analysis was carried out on the filtrate, and used for analysis of the purity (R) and the composition of the product.

TABLE 8 values measured and calculated for Example 7

| | |
|---|---|
| $R^1OH$ = isopentanol Amount of $R^1OH$ = Amount of $R^1$ equivalents ($C_5$) | $m_1 + s_1$ = 846 g 9.6 mol |
| $R^2OH$ = isononanol Amount of $R^2OH$ = Amount of $R^2$ equivalents ($C_9$) | $m_2$ = 346 g 2.4 mol |
| B = dimethyl terephthalate Amount →Amount of ester functions | $m_b$ = 776 g 4 mol 8 mol |
| Expected molar fraction of the $R^1$ functions as a proportion of $R^1$ and $R^2$ functions in the ester mixture (on full incorporation of $R^2$) | 8 mol − 2.4 mol = 5.6 mol corresponding to 70 mol % |
| Ratio $m_1$:$m_2$ | 5.6:2.4, corresponding to 0.7:0.3 |
| $s_1$ | 9.6 mol − (8 mol − 2.4 mol) = 4 mol |
| $T^1 \to T^2$ (liquid phase temperature start→ end) | 123° C. → 166° C. |
| $T^3$ | 190° C. |

TABLE 8-continued

| values measured and calculated for Example 7 | |
|---|---|
| R (purity) | 99.8% |
| Statistical expectation values for complete incorporation of $C_9$: ($C_5/C_5$):($C_5/C_9$):($C_9/C_9$) | 49.0:42.0:9.0 (expected $C_5$ fraction: 70%) |
| Composition according to GC ($C_5/C_5$):($C_5/C_9$):($C_9/C_9$) | 44.3:45.0:10.7 ($C_5$ fraction: 66.8%) |
| | Deviation: $\|49.0 - 44.3\| + \|42.0 - 45.0\| + \|9.0 - 10.7\| = 9.4$ |

This gave 1174 g of worked-up ester mixture 44:45:11

Example 8 (Inventive)

Transesterification of dimethyl terephthalate with isopentanol and isononanol (3:27:70)

Example 8 was carried out as described for Example 1, using dimethyl terephthalate with isopentanol and isononanol. An ester mixture was obtained with a composition ($C_5/C_5$):($C_5/C_9$):($C_9/C_9$) of 3:27:70 according to GC.

Example 9 (Inventive)

Esterification of succinic acid with isopentanol and isononanol (27:51:22)

An apparatus comprising stirring flask with stirrer, immersion tube, water separator with top-mounted intensive condenser, thermometer and 20 cm Raschig ring column was charged with the acid or acid derivative B ($m_b$) and with the alcohols $R^1OH$ ($m_1+s_1$) and $R^2OH$ ($m_2$). The apparatus was flushed for at least one hour with nitrogen (6 l/h) via the immersion tube. Then 0.25 wt % of tetra-n-butyl titanate (Sigma Aldrich, purity>97%) are added, based on the mass of the acid or acid derivative. The reaction was subsequently heated along the boiling temperature from $T^1$ to $T^2$, during which water was removed from the system using the water separator. As soon as reflux could no longer be maintained, at maximum liquid phase temperature $T^2$, cyclohexane ($m_{Azf}$) was added as azeotrope former. As soon as the stoichiometric amount of water had been removed from the reaction (actual amount=$m_{d1}$ archived) and the acid number was less than 0.5 mg KOH/g, the batch was cooled. After cooling to room temperature, the batch was transferred to a stirring flask with stirrer, thermometer, immersion tube, Claisen bridge and receiver flask. The apparatus was flushed for at least one hour with nitrogen (6 l/h) via the immersion tube. The residual excess alcohol was subsequently removed by distillation with application of reduced pressure at $T^3$. As soon as the residual amount of alcohol $R^1OH$ according to GC chromatogram was below 5 mol %, based on the excess amount $s_1$ of the alcohol $R^1OH$, the heating was shut off and the reaction was cooled to 80° C. under reduced pressure and with introduction of nitrogen (20 mbar). The acid number of the flask contents was determined. According to the result, the reaction medium was neutralized by slow dropwise addition of three times the stoichiometric amount of base (10% strength aqueous NaOH solution) and stirred for 15 minutes at 80° C. with introduction of nitrogen (6 l/h). The batch was then slowly evacuated from the ambient pressure to about 1 mbar, whereupon, at about 120° C., it was heated and residual volatiles were separated off by means of nitrogen introduction at constant temperature. The nitrogen flow rate was adjusted such that the pressure did not exceed 20 mbar. As soon as the residual alcohol content according to GC analysis was less than 0.025 area %, the heating was shut off and the product was cooled to 80° C. under reduced pressure and with admission of nitrogen. At this temperature the product was filtered through a Buchner funnel with filter paper and precompacted filter cake of filter aid (D14 Perlite) into a suction bottle by means of reduced pressure. A GC analysis was carried out on the filtrate, and used for analysis of the purity (R) and the composition of the product.

TABLE 9

| Values measured and calculated for Example 9 | |
|---|---|
| $R^1OH$ = isopentanol | $m_1 + s_1$ = 661 g |
| Amount of $R^1OH$ = | 7.5 mol |
| Amount of $R^1$ equivalents ($C_5$) | |
| $R^2OH$ = isononanol | $m_2$ = 720 g |
| Amount of $R^2OH$ = | 5 mol |
| Amount of $R^2$ equivalents ($C_9$) | |
| B = succinic acid | $m_b$ = 591 g |
| (Sigma Aldrich, purity >99%) | 5 mol |
| Amount of B | 10 mol |
| →Amount of ester functions | |
| Expected molar fraction of $R^1$ functions as a proportion of $R^1$ and $R^2$ functions in the ester mixture (on full incorporation of $R^2$) | 10 mol − 5 mol = 5 mol corresponding to 50 mol % |
| Ratio $m_1$:$m_2$ | 0.5:0.5 |
| $s_1$ | 7.5 mol − (10 mol − 5 mol) = 2.5 mol |
| $T^1 \to T^2$ (liquid phase temperature start→end) | 120° C. → 218° C. |
| $m_{d1}$ (distillate reaction) | 184 g (10.2 mol of water) |
| $m_{Azf}$ | 0 g |
| $T^3$ | 177° C. |
| R (purity) | >99.9% |
| Statistical expectation values for complete incorporation of $C_9$: ($C_5/C_5$):($C_5/C_9$):($C_9/C_9$) | 25.0:50.0:25.0 (expected $C_5$ fraction: 50%) |
| Composition according to GC ($C_5/C_5$):($C_5/C_9$):($C_9/C_9$) | 26.9:50.9:22.2 ($C_5$ fraction: 52.3%) |
| | Deviation: $\|26.9 - 25.0\| + \|50.9 - 50.0\| + \|22.2 - 25.0\| = 5.6$ |

This gave 1200 g of worked-up ester mixture.

Example 10 (Inventive)

Esterification of 1,2-cyclohexanedicarboxylic anhydride with isopentanol and isononanol (27:49:24)

Example 10 was carried out as described for Example 9.

TABLE 10

| Values measured and calculated for Example 10 | |
|---|---|
| $R^1OH$ = isopentanol | $m_1 + s_1$ = 264 g |
| Amount of $R^1OH$ = | 3 mol |
| Amount of $R^1$ equivalents ($C_5$) | |
| $R^2OH$ = isononanol | $m_2$ = 288 g |
| Amount of $R^2OH$ = | 2 mol |
| Amount of $R^2$ equivalents ($C_9$) | |
| B = 1,2-cyclohexanedicarboxylic anhydride | $m_b$ = 308 g |
| (Sigma Aldrich, purity 95%) | 2 mol |
| Amount of B | 4 mol |
| →Amount of ester functions | |
| Expected molar fraction of $R^1$ functions as a proportion of $R^1$ and $R^2$ functions in the ester mixture (on full incorporation of $R^2$) | 4 mol − 2 mol = 2 mol corresponding to 50 mol % |
| Ratio $m_1$:$m_2$ | 0.5:0.5 |
| $s_1$ | 3 mol − (4 mol − 2 mol) = 1 mol |
| $T^1 \to T^2$ (liquid phase temperature start→end) | 164° C. → 217° C. |
| $m_{d1}$ (distillate reaction) | 36 g (2 mol of water) |
| $m_{Azf}$ | 0 g |

TABLE 10-continued

Values measured and calculated for Example 10

| | |
|---|---|
| $T^3$ | 160° C. |
| R (purity) | >99.9% |
| Statistical expectation values for complete incorporation of $C_9$: $(C_5/C_5):(C_5/C_9):(C_9/C_9)$ | 25.0:50.0:25.0 (expected $C_5$ fraction: 50%) |
| Composition according to GC $(C_5/C_5):(C_5/C_9):(C_9/C_9)$ | 26.8:48.7:24.4 ($C_5$ fraction: 51.2%) Deviation: \|26.8 − 25.0\| + \|48.7 − 50.0\| + \|24.4 − 25.0\| = 3.7 |

This gave 540 g of worked-up ester mixture.

Example 11 (Inventive)

Esterification of phthalic anhydride with isononanol and isotridecanol Example 11 was carried out as described for Example 9.

TABLE 11

Values measured and calculated for Example 11

| | |
|---|---|
| $R^2OH$ = isononanol Amount of $R^2OH$ = Amount of $R^2$ equivalents ($C_9$) | $m_1 + s_1 = 864$ g 6 mol |
| $R^2OH$ = isotridecanol (Evonik Industries AG, purity >99%) Amount of $R^2OH$ = Amount of $R^2$ equivalents ($C_{13}$) | $m_2 = 801$ g 4 mol |
| B = phthalic anhydride (Sigma Aldrich, purity 99%) Amount of B →Amount of ester functions | $m_b = 592$ g 4 mol 8 mol |
| Expected molar fraction of $R^1$ functions as a proportion of $R^1$ and $R^2$ functions in the ester mixture (on full incorporation of $R^2$) | 8 mol − 4 mol = 4 mol corresponding to 50 mol % |
| Ratio $m_1:m_2$ | 0.5:0.5 |
| $s_1$ | 6 mol − (8 mol − 4 mol) = 2 mol |
| $T^1 \rightarrow T^2$ (liquid phase temperature start→ end) | 212° C. → 240° C. |
| $m_{d1}$ (distillate reaction) | 73 g (4 mol of water) |
| $m_{Azf}$ | 70 g |
| $T^3$ | 200° C. |
| R (purity) | >99.9% |
| Statistical expectation values for complete incorporation of $C_9$: $(C_9/C_9):(C_9/C_{13}):(C_{13}/C_{13})$ | 25.0:50.0:25.0 (expected $C_9$ fraction: 50%) |
| Composition according to GC $(C_9/C_9):(C_9/C_{13}):(C_{13}/C_{13})$ | undeterminable owing to superimposition of signals in GC |

This gave 1580 g of worked-up ester mixture.

Example 12 (Inventive)

Esterification of citric acid with isopentanol and isononanol (54:39:7:0)

Example 12 is carried out as described for Example 9, but the catalyst added, instead of the tetra-n-butyl titanate, was 0.30 wt % of methanesulphonic acid (Sigma Aldrich, purity≥99.5%) (based on the mass of the acid). The reaction in this example was terminated by cooling as soon as the acid number fell below a level of 1.0 mg of KOH per g of the crude product and the expected amount of water of reaction was obtained. Prior to filtration, the crude product was stirred at 80° C. for 60 minutes with 2 wt % of basic aluminium oxide (wt % based on the total mass).

TABLE 12

Values measured and calculated for Example 12

| | |
|---|---|
| $R^1OH$ = isopentanol Amount of $R^1OH$ = Amount of $R^1$ equivalents ($C_5$) | $m_1 + s_1 = 1057$ g 12 mol |
| $R^2OH$ = isononanol Amount of $R^2OH$ = Amount of $R^2$ equivalents ($C_9$) | $m_2 = 346$ g 2.4 mol |
| B = citric acid monohydrate (Sigma Aldrich, purity 99%) Amount of B →Amount of ester functions | $m_b = 841$ g 4 mol 12 mol |
| Expected molar fraction of $R^1$ functions as a proportion of $R^1$ and $R^2$ functions in the ester mixture (on full incorporation of $R^2$) | 12 mol − 2.4 mol = 9.6 mol corresponding to 80 mol % |
| Ratio $m_1:m_2$ | 0.8:0.2 |
| $s_1$ | 12 mol − (12 mol − 2.4 mol) = 2.4 mol |
| $T^1 \rightarrow T^2$ (liquid phase temperature start→ end) | 125° C. → 161° C. |
| $m_{d1}$ (distillate reaction) | 295 g (16.4 mol of water) |
| $m_{Azf}$ | 150 g |
| $T^3$ | 160° C. |
| R (purity) | 99.5% |
| Statistical expectation values for complete incorporation of $C_9$: $(C_5/C_5):(C_5/C_9):(C_9/C_9)$ | 51.2:38.4:9.6:0.8 (expected $C_5$ fraction: 80%) |
| Composition according to GC $(C_5/C_5):(C_5/C_9):(C_9/C_9)$ | 53.9:39.4:6.7: <0.1 ($C_5$ fraction: 82.4%) Deviation: \|53.9 − 51.2\| + \|39.4 − 38.4\| + \|6.7 − 9.6\| + 0.8 = 7.4 |

This gave 1080 g of worked-up ester mixture.

Example 13

Production of plastisols of the inventive ester mixtures 3:27:70 (1, Example 8), 13:46:41 (2, Example 3), 24:51:25 (3, Example 4) and 44:45:11 (4, Example 7)

PVC plastisols were produced, as used, for example, for the manufacture of topcoat films for floorcoverings. The FIGURES in the plastisol formulations are each in mass fractions. The formulations of the polymer compositions are listed in Table 13.

TABLE 13

Plastisol formulation

| | P1 | P2 | P3 | P4 |
|---|---|---|---|---|
| PVC (Vestolit B 7021 - Ultra; from Vestolit) | 100 | 100 | 100 | 100 |
| Ester mixture 3:27:70 (1) | 50 | | | |
| Ester mixture 13:46:41 (2) | | 50 | | |
| Ester mixture 24:51:25 (3) | | | 50 | |
| Ester mixture 44:45:11 (4) | | | | 50 |
| Epoxidized soyabean oil as costabilizer (Drapex 39, from Galata) | | | | |
| Heat stabilizer based on Ca/Zn (Mark CZ 149, from Galata) | 3 2 | 3 2 | 3 2 | 3 2 |

Figures in phr (phr = parts per hundred parts resin); P: Plastisol

Figures in phr (phr=carts per hundred parts resin); P: Plastisol

The ester mixtures were conditioned at 25° C. prior to addition. First the liquid constituents and then the pulverulent constituents were weighed out into a PE cup. The mixture was stirred manually with an ointment spatula in such a way that no unwetted powder was present any longer. The mixing beaker was then clamped into the clamping device of a dissolver stirrer. Before the stirrer was immersed into the mixture, the rotational speed was set to 1800 revolutions per minute. After the stirrer was switched on, the mixture was stirred until the temperature on the digital display of the thermal sensor reached 30.0° C. This ensured that the plastisol was homogenized at a defined energy input. Thereafter, the plastisol was immediately conditioned to 25.0° C. in a conditioning cabinet for further studies.

Example 14

Gelling Temperature of Plastisols 1 to 4 (P1-P4)

The gelation characteristics of the plastisols were examined with a Physica MCR 101 in oscillation mode using a parallel plate analysis system (PP25), which was operated under shear stress control. An additional heating hood was connected to the system in order to achieve a homogeneous heat distribution and uniform sample temperature.

The following parameters were set:

| Mode: | Temperature gradient |
|---|---|
| Start temperature | 25° C. |
| End temperature | 180° C. |
| Heating/cooling rate | 5° C./min |
| Oscillation frequency | 4-0.1 Hz logarithmic ramp |
| Cycle frequency omega: | 10 1/s |
| Number of measurement points: | 63 |
| Measurement point duration: | 0.5 min |
| Automatic gap adjustment | F: 0 N |
| Constant measurement point duration | 0.5 mm |
| Gap width | |

Analysis Procedure:

The spatula was used to apply a few grams of the plastisol to be analysed, free from air bubbles, to the lower plate of the analysis system. In doing so, it was ensured that, after the analysis system had been assembled, it was possible for some plastisol to exude uniformly out of the analysis system (not more than about 6 mm in any direction). The heating hood was subsequently positioned over the sample and the analysis was started. What is called the complex viscosity of the plastisol was determined after 24 h (storage of the plastisol at 25° C. in a temperature control cabinet from Memmert) as a function of temperature.

A significant increase in the complex viscosity was viewed as a measure of the gelling. As a value for comparison, therefore, the temperature on attainment of a plastisol viscosity of 1000 Pa·s was used.

TABLE 14

Gelling of plastisols 1 to 4 after 24 h, temperature in ° C. on attainment of a plastisol viscosity of $10^3$ Pa · s (in short: Gelling temperature)

| | Gelling temperature [° C.] |
|---|---|
| Diisononyl terephthalate (DINT) | 109 |
| P1 (3:27:70) | 92 |
| P2 (13:46:41) | 83 |
| P3 (24:51:25) | 80 |
| P4 (44:45:11) | 76 |
| Diisopentyl terephthalate (DPT) | 70 |

P: Plastisol

Plotted in the FIGURE for the inventive ester mixtures 1 to 4 is the gelling temperature of the plastisol from Table 14 against the associated volatility of the film comprising the same ester mixture (from Example 16, Table 15).

Example 15

Production of Films of the Inventive Ester Mixtures

The plastisols produced in Example 13 were each processed into films 1 mm thick.

For this purpose, high-gloss release paper (from Sappi, Italy) was first trimmed to a size of 30×44 cm and inserted in the clamping frame of the LTSV coating device for the Mathis oven. The clamping frame was then placed on the guide frame, the Mathis oven (type LTF) was set to 200° C., and the frame was preheated for 15 seconds after the aforementioned temperature had been reached. The doctor was then placed into the clamping means and the doctor gap was adjusted via preliminary tests in such a way that the film thickness after the end of gelling was 1 mm (+/−0.05 mm). An adhesive strip was mounted on the front edge of the paper in order to collect excess paste. The paste was subsequently applied ahead of the doctor, and was spread by the guide frame with the doctor being drawn over the clamped release paper (at a rate of about 3 m/min). Thereafter the doctor was removed and the adhesive strip with the excess paste was taken off. The melting roller was subsequently lowered and the clamping frame was inserted into the oven. After gelling (2 minutes at 200° C.), the frame was removed from the oven again and, after cooling, the film was removed from the paper.

For each formulation under test, three circles of 10 cm² were punched from the films. In addition, the circles were cut into radially with scissors (2 cuts each of 5 mm). The circles were conditioned for half an hour in a desiccator (filled with orange KC drying beads) and then weighed.

Example 16

Loss of Mass on Activated Carbon Storage for Films 1-4 (F1-F4)

Tin cans (1 l, tall shape) were punctured in the lid in order that exchange of pressure could take place. The bases of the tin cans were covered with 120 ml of activated carbon. The activated carbon used in this test (No. 774408 from Roth) was dried beforehand in an evaporation dish for 6 hours in a drying cabinet at 100+/−1° C. and was used after brief cooling. The first sample circle was placed onto the middle of the activated carbon. A further 120 ml of activated carbon were placed onto the sample circle. In total, the tin cans were filled with 480 ml of activated carbon and 3 sample circles in layers. The lid of the tin cans was placed onto the cans without pressure.

The filled tin cans were stored in a temperature control cabinet at 100+/−1° C. for 3 days. After the storage, the activated carbon was removed from the circles by means of an analysis brush, and the circles were stored in a desiccator for 30 minutes for cooling and then weighed.

After the weighing, the sample circles were layered again with activated carbon back in the tin cans. Care was taken here to ensure that the sample circles were again assigned to the same activated carbon and the same can. The cans were placed in the temperature control cabinet again. After a total of 7 days, the samples were then weighed again as already described.

The percentage change in mass of each sample circle was calculated, and the mean over the 3 circles for each formulation was calculated.

TABLE 15

Loss of mass on activated carbon storage in mass % (volatility)

| | Volatility (mass %) | |
|---|---|---|
| | 3 days | 7 days |
| Diisononyl terephthalate (DINT) | 4.0 | 5.4 |
| F1 (3:27:70) | 4.9 | 8.2 |
| F2 (13:46:41) | 6.2 | 11.0 |
| F3 (24:51:25) | 9.3 | 15.3 |
| F4 (44:45:11) | 13.9 | 20.8 |
| Diisopentyl terephthalate (DPT) | 20.5 | 26.2 |

F: Film

The FIGURE, for inventive ester mixtures 1 to 4, plots the gelling temperature of the plastisol from Table 14 of Example 14 against the associated volatility of the film containing the same ester mixture (from Table 15).

European patent application EP15155564.6 filed Feb. 18, 2015, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for producing an ester mixture, the process comprising:
reacting $A(COOH)_{x+1}$ or derivatives thereof, which contain no ester group COOR having a radical R whose alcohol ROH has a higher boiling point at a defined pressure than an alcohol $R^1OH$ at the defined pressure, with the alcohol $R^1OH$ and an alcohol $R^2OH$ in a reaction mixture comprising a catalyst, said reaction mixture being heated at boiling, to obtain a product mixture;
removing from the product mixture a portion of a residual amount of added alcohol $R^1OH$ that does not react with the compound of formula: $A(COOH)_{x+1}$ or derivatives thereof; and then
destroying the catalyst to obtain an ester mixture comprising $A(COOR^1)(COOR^1)_x$, $A(COOR^1)(COOR^2)_x$, $A(COOR^2)(COOR^1)_x$ and $A(COOR^2)(COOR^2)_x$,
wherein:
a molar equivalent amount $(m_1+s_1)$ of the alcohol $R^1OH$ is added to the reaction mixture, and a molar equivalent amount $(m_2)$ of the alcohol $R^2OH$ is added to the reaction mixture;
$(m_1)$ represents a theoretical molar equivalent of the alcohol $R^1OH$ that reacts with the compound of formula: $A(COOH)_{x+1}$ or derivatives thereof, on assumption that all of the alcohol $R^2OH$ reacts with the compound of formula: $A(COOH)_{x+1}$ or derivatives thereof and is incorporated into the ester mixture;
$(s_1)$ is greater than zero, and represents a theoretical molar equivalent of the residual amount of the alcohol $R^1OH$ that does not react with the compound of formula: $A(COOH)_{x+1}$ or derivatives thereof, on assumption that all of the alcohol $R^2OH$ reacts with the compound of formula: $A(COOH)_{x+1}$ or derivatives thereof and is incorporated into the ester mixture;
A is an aromatic, alicyclic or aliphatic radical;
x is 1 or 2;
$R^1$ and $R^2$ independently of one another are substituted or unsubstituted aryl radicals or linear or branched, substituted or unsubstituted alkyl radicals having 3 to 20 carbon atoms, the alcohol $R^1OH$ having a lower boiling point at a defined pressure than the alcohol $R^2OH$ at the same pressure;
the removing of the portion of the alcohol $R^1OH$ from the product mixture lowers an amount of the alcohol $R^1OH$ in the product mixture to less than 20 mol % of the residual amount $(s_1)$ of the alcohol $R^1OH$, before the catalyst is destroyed; and
for x=1,
a molar fraction of the esters $A(COOR^1)(COOR^1)_x$, $A(COOR^1)(COOR^2)_x$, $A(COOR^2)(COOR^1)_x$ and $A(COOR^2)(COOR^2)_x$ in the ester mixture deviates by less than 12 points from a statistically determined expectation value which arises when assuming that the entire molar equivalent $(m_2)$ of the alcohol $R^2OH$ reacts with the compound of formula: $A(COOH)_{x+1}$ or derivatives thereof, said 12 points corresponding to a sum total of all amounts of differences between statistical expectation value and actual molar fraction of each individual ester in the ester mixture when a sum total of molar fractions of esters in the ester mixture adds up to 100, or
for x=2,
a molar fraction of the esters $A(COOR^1)(COOR^1)_x$, $A(COOR^1)(COOR^2)_x$, $A(COOR^2)(COOR^1)_x$ and $A(COOR^2)(COOR^2)_x$ in the ester mixture deviates by less than 25 points from a statistically determined expectation value which arises when assuming that the entire molar equivalent $(m_2)$ of the alcohol $R^2OH$ reacts with the compound of formula: $A(COOH)_{x+1}$ or derivatives thereof, said 25 points corresponding to a sum total of all amounts of differences between statistical expectation value and actual molar fraction of each individual ester in the ester mixture when a sum total of molar fractions of esters in the ester mixture adds up to 100.

2. The process according to claim 1, wherein the compound of formula: $A(COOH)_{x+1}$ or derivatives thereof is at least one selected from the group consisting of phthalic acid, terephthalic acid, isophthalic acid, 1,2-, 1,3- or 1,4-cyclohexanedicarboxylic acid, adipic acid, sebacic acid, maleic acid, succinic acid, furandicarboxylic acid and citric acid.

3. The process according to claim 1, wherein $R^1$ and $R^2$ independently of one another are alkyl radicals which contain 3 to 20 carbon atoms.

4. The process according to claim 1, wherein $R^1$ and $R^2$ independently of one another are alkyl radicals which contain 3 to 20 carbon atoms, said alkyl radicals having no other functional group.

5. The process according to claim 3, wherein $R^1$ and $R^2$ independently of one another are selected from the group consisting of propyl, butyl, tert-butyl, isobutyl, 2-methylbutyl, 3-methylbutyl, n-pentyl, isopentyl, hexyl, heptyl, isoheptyl, octyl, isooctyl, 2-ethylhexyl, nonyl, n-nonyl, isononyl, decyl, isodecyl, 2-propylheptyl, undecyl and tridecyl radicals.

6. The process according to claim 1, wherein boiling points of the alcohols $R^1OH$ and $R^2OH$ differ by at least 10° C.

7. The process according to claim 1, wherein the amount $(s_1)$ is less than an amount $(m_1+m_2)$, is greater than an amount $0.05 \cdot (m_1+m_2)$, or both.

8. The process according to claim 1, wherein the removing of the portion of the alcohol $R^1OH$ from the product mixture lowers the amount of the alcohol $R^1OH$ in the product mixture to less than 15 mol % of the amount $(s_1)$, before the catalyst is destroyed.

9. The process according to claim 1, wherein the molar fraction of the esters $A(COOR^1)(COOR^1)_x$, $A(COOR^1)(COOR^2)_x$, $A(COOR^2)(COOR^1)_x$ and $A(COOR^2)(COOR^2)_x$ in the ester mixture, for x=1, deviates by less than 10 points from the statistically determined expectation value which arises when assuming that the entire molar equivalent ($m_2$) of the alcohol $R^2OH$ reacts with the compound of formula: $A(COOH)_{x+1}$ or derivatives thereof, said 10 points corresponding to the sum total of all amounts of differences between statistical expectation value and actual molar fraction of each individual ester in the ester mixture when the sum total of molar fractions of esters in the ester mixture adds up to 100.

10. The process according to claim 1, wherein the molar fraction of the esters $A(COOR^1)(COOR^1)_x$, $A(COOR^1)(COOR^2)_x$, $A(COOR^2)(COOR^1)_x$ and $A(COOR^2)(COOR^2)_x$ in the ester mixture, for x=2, deviates by less than 15 points from the statistically determined expectation value which arises when assuming that the entire molar equivalent ($m_2$) of the alcohol $R^2OH$ reacts with the compound of formula: $A(COOH)_{x+1}$ or derivatives thereof, said 15 points corresponding to the sum total of all amounts of differences between statistical expectation value and actual molar fraction of each individual ester in the ester mixture when the sum total of molar fractions of esters in the ester mixture adds up to 100.

11. The process according to claim 1, wherein:
the compound of formula: $A(COOH)_{x+1}$ or derivatives thereof is phthalic acid, terephthalic acid or isophthalic acid; and
after an optional work-up the ester mixture is subsequently hydrogenated.

12. An ester mixture produced by the process according to claim 1.

13. The process according to claim 1, further comprising: controlling a quantitative distribution of esters in the ester mixture.

14. A polymer plasticizer, comprising the ester mixture according to claim 12.

15. The polymer plasticizer according to claim 14, which is adapted to function as a plasticizer for a PVC.

16. An article, comprising the polymer plasticizer of claim 14, wherein said article is selected from the group consisting of a synthetic leather, a floorcovering, a roofing membrane, an underbody protection, a fabric coating, a cable, a wire insulation, a hose, an extruded article, a film, an automotive interior article, a wallcovering, a liquid ink, a toy, a contact sheet, a food packaging and a medical article.

17. A composition, comprising:
the ester mixture according to claim 12; and
at least one selected from the group consisting of a polyvinyl chloride, a copolymer of vinyl chloride with vinyl acetate, a copolymer of vinyl chloride with butyl acrylate, a polyalkyl methacrylate (PAMA), a polyvinyl butyral (PVB), a polyurethane, a polysulfide, a polylactic acid (PLA), a polyhydroxybutyral (PHB) and a nitrocellulose.

18. A composition, comprising the polymer plasticizer of claim 14, wherein said composition is selected from the group consisting of an adhesive, a sealant, a coating material, a paint, an ink, a plastisol, and a foam.

19. A composition, comprising the ester mixture of claim 12 and a polymer.

20. The process according to claim 1, wherein the compound of formula: $A(COOH)_{x+1}$ is not terephthalic acid.

21. The process according to claim 1, comprising reacting a derivative of $A(COOH)_{x+1}$ with the alcohol $R^1OH$ and an alcohol $R^2OH$.

* * * * *